US008932367B2

(12) United States Patent
Smith

(10) Patent No.: US 8,932,367 B2
(45) Date of Patent: Jan. 13, 2015

(54) SHOCK ABSORBING IMPLANTABLE LIMB PROSTHETIC

(71) Applicant: Larry N. Smith, Gainesville, FL (US)

(72) Inventor: Larry N. Smith, Gainesville, FL (US)

( * ) Notice: Subject to any disclaimer, the term of this patent is extended or adjusted under 35 U.S.C. 154(b) by 120 days.

(21) Appl. No.: 13/766,044

(22) Filed: Feb. 13, 2013

(65) Prior Publication Data

US 2014/0228896 A1    Aug. 14, 2014

(51) Int. Cl.
*A61B 17/04*      (2006.01)
*A61B 17/86*      (2006.01)
*A61F 2/08*       (2006.01)
*A61F 2/78*       (2006.01)
*A61F 2/80*       (2006.01)

(52) U.S. Cl.
CPC .................................. *A61B 17/8605* (2013.01)
USPC .................. 623/33; 623/32; 623/36; 606/305

(58) Field of Classification Search
CPC ...................... A61F 2002/7685; A61F 13/0273
USPC ........................................ 623/32–38; 606/305
See application file for complete search history.

(56) References Cited

U.S. PATENT DOCUMENTS

| 3,947,897 | A | 4/1976 | Owens |
|---|---|---|---|
| 3,992,725 | A | 11/1976 | Homsy |
| 4,007,494 | A | 2/1977 | Sauer |
| 4,547,912 | A | 10/1985 | Sherva-Parker |
| 4,634,446 | A | 1/1987 | Kristinsson |
| 4,743,264 | A | 5/1988 | Sherva-Parker |
| 4,778,470 | A | 10/1988 | Antebi |
| 4,781,720 | A | 11/1988 | Sherva-Parker |
| 5,041,137 | A | 8/1991 | Nemoshkalov |
| 5,507,835 | A | 4/1996 | Jore |
| 5,531,793 | A | 7/1996 | Kelman et al. |
| 5,571,208 | A | 11/1996 | Caspers |
| 5,591,233 | A | 1/1997 | Kelman et al. |
| 5,725,580 | A | 3/1998 | Cloutier et al. |
| 5,879,386 | A | 3/1999 | Jore |
| 5,894,181 | A | 4/1999 | Imlach |
| 5,904,722 | A | 5/1999 | Caspers |

(Continued)

FOREIGN PATENT DOCUMENTS

| WO | WO 02-26158 | 4/2002 |
|---|---|---|
| WO | WO 2010-070614 | 6/2010 |

OTHER PUBLICATIONS

Attinger, C.E., et al., "Angiosomes of the Foot and Ankle and Clinical Implications for Limb Salvage: Reconstruction, Incisions, and Revascularization," *Plastic and Reconstructive Surgery*, vol. 117, No. 7S, Jun. 2006 Supplement, pp. 261S-293S.

(Continued)

*Primary Examiner* — Sameh Boles
(74) *Attorney, Agent, or Firm* — Saliwanchik, Lloyd & Eisenschenk

(57) ABSTRACT

The subject invention pertains to embodiments of a device for implantation into a residual amputated limb. More specifically, the subject invention provides one or more embodiments of an implantable force-distribution support that can be installed onto the terminal end of a bone or bone stump in a residual limb. The force-distribution support can restore the natural hydrodynamic system of the skeleton and can re-engage the axial skeleton as a factor in absorbing forces of ambulation. Embodiments can include a support bracket that can be attached to the terminal bone end to which a resilient-support can be attached to protect residual tissue from compression forces.

37 Claims, 17 Drawing Sheets

(56) References Cited

U.S. PATENT DOCUMENTS

| | | | |
|---|---|---|---|
| 6,123,716 | A | 9/2000 | Augustine et al. |
| 6,132,468 | A | 10/2000 | Mansmann |
| 6,197,065 | B1 | 3/2001 | Martin et al. |
| 6,224,623 | B1 | 5/2001 | Augustine et al. |
| 6,355,067 | B1 | 3/2002 | Bloebaum |
| 6,387,096 | B1 | 5/2002 | Hyde, Jr. |
| 6,482,238 | B1 | 11/2002 | Grundei |
| 6,599,321 | B2 | 7/2003 | Hyde, Jr. |
| 6,709,466 | B1 | 3/2004 | Grundei |
| 6,923,832 | B1 | 8/2005 | Sharkey et al. |
| 7,044,953 | B2 | 5/2006 | Capanni |
| 7,101,374 | B2 | 9/2006 | Hyde, Jr. |
| 7,223,293 | B2 | 5/2007 | Kristensen |
| 7,302,296 | B1 | 11/2007 | Hoffer |
| 7,374,577 | B2 | 5/2008 | Kim et al. |
| 7,850,740 | B2 | 12/2010 | Cox et al. |
| 7,909,883 | B2 | 3/2011 | Sidebotham |
| 7,922,773 | B1 | 4/2011 | Kuiken |
| 7,967,869 | B2 | 6/2011 | Schulman et al. |
| 7,972,384 | B2 | 7/2011 | Parsell |
| 2004/0193286 | A1 | 9/2004 | Grundei |
| 2005/0101693 | A1 | 5/2005 | Arbogast et al. |
| 2005/0119755 | A1 | 6/2005 | Kristensen |
| 2005/0171604 | A1 | 8/2005 | Michalow |
| 2005/0240283 | A1 | 10/2005 | Kania |
| 2006/0064169 | A1 | 3/2006 | Ferree |
| 2006/0293762 | A1 | 12/2006 | Schulman et al. |
| 2007/0150070 | A1 | 6/2007 | Kim et al. |
| 2007/0162150 | A1 | 7/2007 | Fago et al. |
| 2009/0005820 | A1 | 1/2009 | Bloebaum et al. |
| 2009/0198342 | A1 | 8/2009 | Parsell |
| 2009/0254196 | A1 | 10/2009 | Cox et al. |
| 2010/0152864 | A1 | 6/2010 | Isaacson et al. |
| 2010/0203155 | A1 | 8/2010 | Wei et al. |
| 2010/0268232 | A1 | 10/2010 | Betz et al. |
| 2011/0015761 | A1* | 1/2011 | Celebi et al. .................. 623/32 |
| 2011/0054408 | A1 | 3/2011 | Wei et al. |
| 2011/0144756 | A1* | 6/2011 | Bickley et al. ............. 623/18.11 |
| 2012/0116539 | A1* | 5/2012 | Armstrong et al. ............. 623/36 |

OTHER PUBLICATIONS

Dillingham, T.R., et al., "Use and Satisfaction with Prosthetic Devices Among Persons with Trauma-Related Amputations," *American Journal of Physical Medicine & Rehabilitation,* Aug. 2001, vol. 80, No. 8, pp. 563-571.

Gray, H., *Gray's Anatomy,* 1901, reprinted 1995, Barnes and Noble, 15th Ed., pp. 562-570.

Imanishi, N., et al., "Anatomical Study of Cutaneous Venous Flow of the Sole," *Plastic and Reconstructive Surgery,* Dec. 2007, vol. 120, No. 7, pp. 1906-1910.

Nllic Staff, "Amputation Statistics by Cause: Limb Loss in the United States," National Limb Loss Information Center Fact Sheet, Rev. 2008.

Oh, S.J., et al., "Weight-Bearing Plantar Reconstruction Using Versatile Medial Plantar Sensate Flap," *Journal of Plastic, Reconstructive & Aesthetic Surgery,* 2011, vol. 64, pp. 248-254.

Russell, W.L., et al., "Limb Salvage Versus Traumatic Amputation," *Annals of Surgery,* May 1991, vol. 213, No. 5, pp. 473-480.

Stansbury, L.G., et al., "Amputations in U.S. Military Personnel in the Current Conflicts in Afghanistan and Iraq," *Journal of Orthopaedic Trauma,* Jan. 2008, vol. 22, No. 1, pp. 43-46.

Vasquez, T., et al., "Anatomic Study of Blood Supply of the Dorsum of the Foot and Ankle," *Arthroscopy: The Journal of Arthroscopic and Related Surgery,* Mar. 2006, vol. 22, No. 3, pp. 287-290.

Waters, P.M., et al., "Use of an Osteocutaneous Plantar Free Flap for Salvage of a Below-the-Knee Amputation in a Child: A Case Report," *Journal of Bone and Joint Surgery,* Jul. 1997, vol. 79, No. 7, pp. 1073-1075.

Yamada, T., et al., "Variations of the Arterial Anatomy of the Foot," *The American Journal of Surgery,* Aug. 1993, vol. 166, No. 2, pp. 130-135.

Yavari, M., et al., "Comparison of Sole to Palm Reconstruction Using the Combined Medical Plantar and Medial Pedis Free Flaps and Abdominal Pedicle Flap for Extensive Palm Injuries," *Acta Medica Iranica,* 2010, vol. 48, No. 4, pp. 214-217.

Zhang, M., et al., "Clinical Investigation of the Pressure and Shear Stress on the Trans-Tibial Stump With a Prosthesis," *Medical Engineering & Physics,* Apr. 1998, vol. 20, No. 3, pp. 188-198.

Ziegler-Graham, K., et al., "Estimating the Prevalence of Limb Loss in the United States: 2005 to 2050," *Archives of Physical Medicine and Rehabilitation,* Mar. 2008, vol. 89, No. 3, pp. 422-429.

Swanson, A.B., "Improving the End-Bearing Characteristics of Lower Extremity Amputation Stumps—A Preliminary Report," *JACPOC,* 1966, pp. 1-8, vol. 5, No. 5.

Swanson, A.B., "Bone Overgrowth in the Juvenile Amputee and Its Control by the Use of Silicone Rubber Implants," *JACPOC,* 1969, pp. 1-9, vol. 8, No. 5.

Meyer, L.C. et al., "The Use of Porous, High-Density Polyethylene Caps in the Prevention of Appositional Bone Growth in the Juvenile Amputee: A Preliminary Report," *JACPOC,* 1975, pp. 1-5, vol. 14, No. 9.

"Sutter Lesser Metatarsal Cap" Amendment to 510(K) report submitted to the Food & Drug Administration (Jul. 30, 1986) SutterBiomedical, Inc., San Diego, CA.

* cited by examiner

SHOCK ABSORBING IMPLANTABLE LIMB PROSTHETIC

BACKGROUND OF INVENTION

Limb amputations have been a part of human existence since the earliest beginnings. While the reasons for such traumas vary and have changed over the centuries, limb amputations continue to account for a significant portion of major injuries each year. Currently, over 1.6 million people currently live with the loss of a limb and that number is expected to double by 2050. Over 30% of those people have lost a lower extremity. The difficulties of living and working with a prosthetic limb remain almost the same as they have from the earliest days. Various types of prosthetic limbs have been devised over time to assist individuals with lower limb amputations. Today's prosthetic limbs are highly sophisticated with a vast array of light-weight materials and ergonomic designs to facilitate normal walking patterns.

Notwithstanding all of the improvements to external prosthetic limbs, a lower-extremity amputee still faces the difficulty of being able to adjust to using a new prosthesis quickly. Some patients can take years to functionally adapt to a prosthesis. This is because, regardless of how many improvements are made to external prosthetic devices, they still operate by attachment to a residual limb having a blunt-ended terminal bone. For a non-amputee, the forces associated with ambulation are distributed throughout the musculo-skeletal system, particularly of the legs and feet. The joints between the bones, which contain a non-compressible fluid, act like hydrodynamic dampers or shock absorbers that absorb the kinetic energy associated with ambulation and distribute it throughout the musculo-skeletal system. For an amputee, the loss of one or more joints means that forces can no longer be adequately distributed and usually become intensified at the terminal end of the residual limb. With the loss of the fluid filled ankle joint in below-knee amputations and the loss of the knee joint and ankle joint in above the knee amputations, the normal non-compressible-fluid hydrodynamic system of the legs and axial skeleton is lost. As a result, expecting an amputee to walk on a boney stump inserted into a prosthetic socket can be unreasonable, as evidenced by the difficulty often experienced by amputees with transitioning to and using a new prosthesis. Thus, it is important to consider reconstruction of the hydrodynamic function of the skeletal system after amputation.

There is a need to overcome the dysfunctional, post-surgical, anatomical deficiencies exhibited by most currently used prosthetic devices. More specifically, there is a need for a system that replaces that portion of the non-compressible-fluid hydrodynamic system lost with amputation. Such a system should distribute the weight and forces of ambulation over a larger area of the residual limb end and reestablish the role of the axial skeletal system in ambulation. Ideally, such improvements will provide long term solutions and facilitate better use of a variety of external prosthetic devices.

BRIEF SUMMARY

Ambulation exerts considerable force on the body, particularly the bone and joints of the lower body. Under normal circumstances, this force, caused by body weight, gravity, momentum, and other factors, is absorbed and distributed by the musculo-skeletal system of the body. The joints within this system, which also contain a non-compressible synovial fluid, inhibit contact between individual bones and assume the role of hydrodynamic dampers that reduce the forces exerted on individual parts of the musculo-skeletal system. Thus, much of the musculo-skeletal system is dependent on hydrodynamics to reduce the amount of force applied to any one area of the body.

Lower-limb amputees are at a specific disadvantage because their musculo-skeletal system has been compromised by the loss of some these shock-absorbing hydrodynamic structures. For amputees, the forces associated with standing or ambulation become problematic because they can no longer be adequately absorbed and dissipated throughout their entire musculo-skeletal system. On an amputated limb, these forces become intensified, particularly at the terminal end where the truncated bone is surrounding by only the residual soft tissue. As a result, forces exerted on the amputated limb can become isolated on a relatively small, single-point on the soft tissues around the terminal bone end. Only the quality of the residual tissues in the limb can affect how much force is dissipated, which is usually very minimal. But, even with high-quality residual tissue over and surrounding the terminal bone end, the forces of ambulation can be only partially distributed, making ambulation difficult and often painful for amputees, even under the best circumstances.

In accordance with the invention, the problems associated with the lack of force distribution on an amputated limb, particularly where a terminal bone end applies intense forces to residual tissues, is solved by an implantable device capable of distributing those forces over a larger surface area. In particular, the embodiments of the subject invention provide novel and highly effective devices for distributing weight and the forces caused by ambulation over more of the residual tissue and boney stump. More specifically, the embodiments of the subject invention provide an implantable, orthopedic, hydrodynamic amputee prosthesis designed to distribute the weight and force of walking over a large area of the terminal surface of the residual limb as well as throughout the musculo-skeletal system. Advantageously, the devices and methods disclosed herein can improve the dynamic interaction between the newly reconstructed residual limb and an external walking prosthesis and can prevent the otherwise dysfunctional boney stump from receiving all the weight of ambulation on a single point.

Embodiments of the subject invention provide a device having a resilient-support, such as, for example, an elastomeric solid, semi-solid, gel, liquid, non-homogenous material, or a combination thereof, that can be implanted onto the terminal end of an amputated bone. The resilient-support can provide shock absorption and a larger surface area over which the forces exerted on the residual limb can be distributed so that it can protect the surrounding residual tissues from those forces, reducing pain and discomfort. Thus, the resilient-support acts similar to a natural, fluid-filled joint by allowing the forces to be absorbed and directed to the bone which can reestablish the axial skeleton as a mechanism for coping with the weight and force of ambulation instead of forcing this role on the residual tissues. This system provides for a more functional weight bearing residual limb. Embodiments of the device can provide natural hydraulic damping and walking dynamics to a residual limb, and, more critically, can restore the role of the axial skeleton in absorbing the dynamic forces of ambulation.

As with many implanted devices, it is possible that these embodiments may not be lifetime devices. It is anticipated that additional unplanned surgeries on the residual limb may be necessary because of complications, discomfort, or unacceptable cosmetic outcomes. These additional surgeries can include implant removal with or without replacement, or they can include other elected surgical procedures to alter the device. Advantageously, the embodiments of the subject invention can be modular, allowing for certain components to be removed, replaced, or upgraded, if necessary, without removal of the entire device. The devices disclosed herein can provide a patient with a more convenient and comfortable alternative implanted prosthetic device that reduces overall stress on the residual limb, as well as the entire body.

BRIEF DESCRIPTION OF DRAWINGS

In order that a more precise understanding of the above recited invention can be obtained, a more particular description of the invention, briefly described above, will be rendered by reference to specific embodiments that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which.

DETAILED DISCLOSURE

Figure 1A:
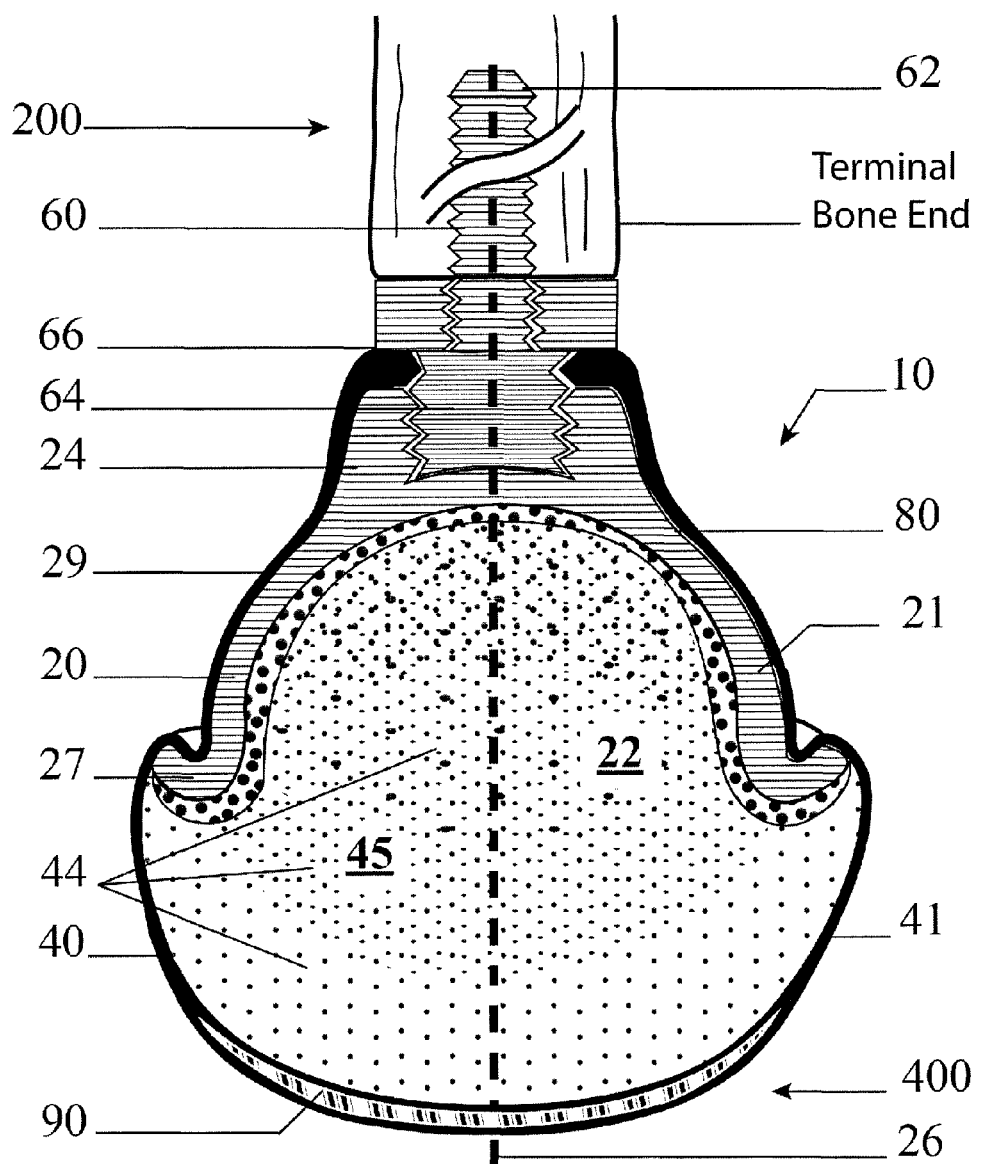
FIG. 1A is a cross-sectional view of one embodiment of a force-distribution support structure (FDSS) having a bell-shaped support bracket, according to the subject invention. This view illustrates the FDSS implanted on a terminal bone end with an embodiment of a resilient-support operably attached to the support bracket.

The subject invention describes embodiments of a device for implantation into the residual end of an amputated limb. More specifically, the subject invention provides one or more embodiments of an implantable force-distribution support structure (FDSS) that can be fixed to the terminal bone end or bone stump in a residual limb. The FDSS can operate similarly to the natural hydrodynamic system of the skeleton, replacing, at least partially, what was lost with an amputation.

The following description will disclose that the embodiments of the subject invention are particularly useful for lower extremity amputations, in particular when used with external devices to provide ambulation to an amputee. However, a person with skill in the art will be able to recognize numerous other uses, such as, for example, upper body amputations, that would be applicable to the devices and methods of the subject invention. Thus, while the subject application describes embodiments for specific uses with residual leg limbs, other modifications and uses that would be apparent to a person with skill in the art and having benefit of the subject disclosure are contemplated to be within the scope of the present invention.

In the description that follows, a number of terms used in relation to the field of surgical amputations are utilized. In order to provide a clear and consistent understanding of the specification and claims, including the scope to be given such terms, the following definitions are provided.

The term "amputee" as used herein, describes an animal, including mammals to which the systems and methods of the present invention are applied. Mammalian species that can benefit from the disclosed systems and methods include, but are not limited to, humans, apes, chimpanzees, orangutans, and monkeys; domesticated animals (e.g., pets) such as dogs and cats; large animals such as cattle, horses, goats, and sheep; and any wild animal for veterinary or tracking purposes.

For literary convenience, the term "ambulation" is used herein to refer to any motion that exerts force on the body, including, but not limited to, standing, walking, running, jogging, climbing, or the like.

The term "anchoring screw" is used herein for literary convenience to refer to any device that can be used to secure components of the subject invention to bone or other tissues within the body. Such devices can include, but are not limited to, medullary screws, cortico-medullary screws, intramedullary screws, entramedullary screws, hollow cortical screws, self-tapping screws, non-self-tapping screws, compression plate compatible screws, and similar devices. It can also include, but is not limited to, adhesives, bone-pastes, tapes, or other types of biocompatible substances or devices for attaching components to bone or other tissues.

Also, as used herein, and unless otherwise specifically stated, the terms "operable communication," "operable connection," "operably connected," and "cooperatively engaged" or derivations thereof mean that the particular elements are connected in such a way that they cooperate to achieve their intended function or functions. The connection or engagement may be direct, or indirect, physical or remote.

Finally, reference is made throughout the application to the "proximal end" and "distal end" of the device. As used herein, the proximal end is the end of the device having a stem that when implanted, is nearest the hip joint of an amputee. Conversely, the distal end of the device is the end having a resilient-support that, when implanted, is closest to the terminal end of the residual limb of an amputee.

The present invention is more particularly described in the following embodiments that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached figures, which show certain embodiments of the subject invention, it can be seen that the subject invention, in general, comprises a support bracket 20, a resilient-support 40, and a stem 60 that, when operatively connected, create an implantable prosthetic device force-distribution support structure 10. In general, the support bracket provides a structure that facilitates normal ambulation with an external prosthetic device, while the resilient-support provides proper weight and force distribution, both of which are operably connected to a terminal bone end by the stem.

Figure 2:
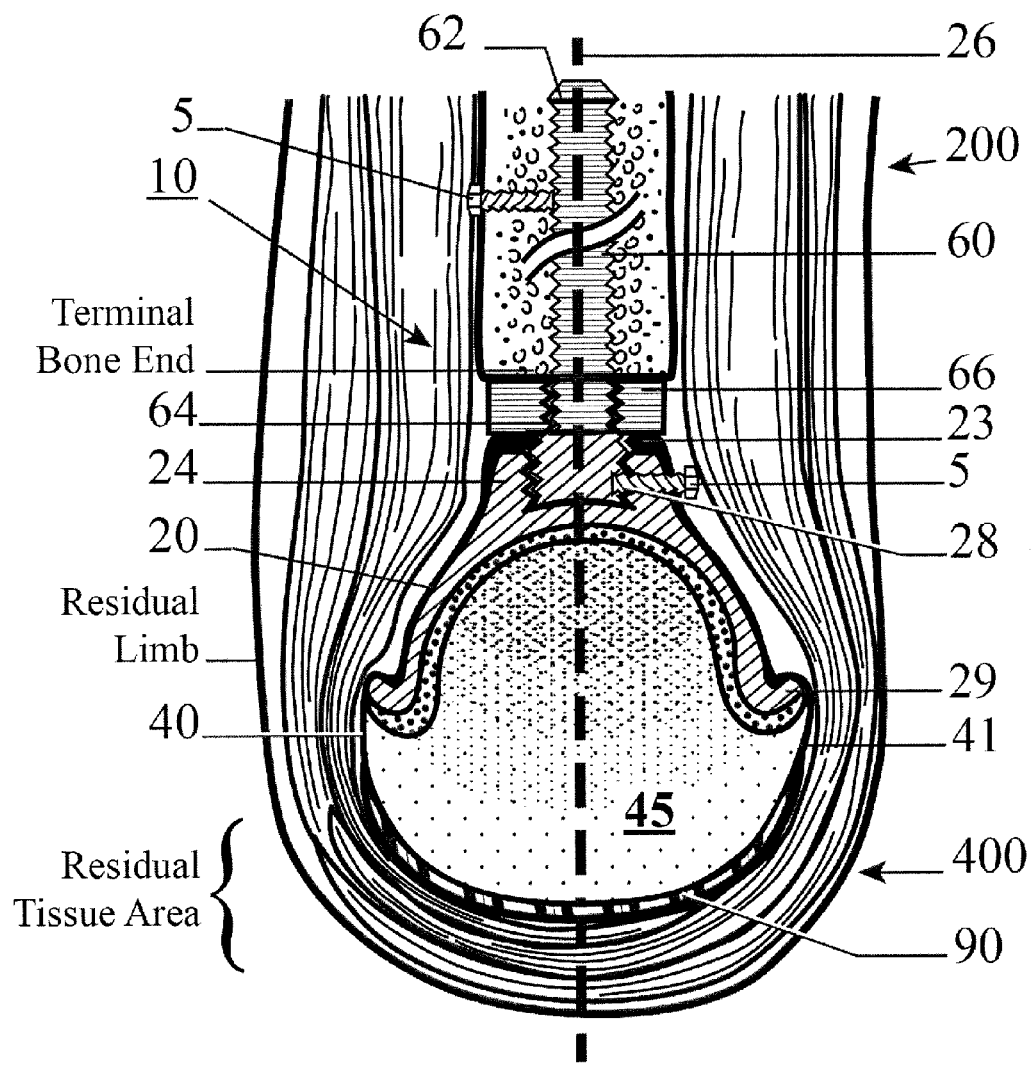
FIG. 2 illustrates a cross-section of front plan view of an embodiment of a FDSS, according to the subject invention, implanted onto the terminal bone end within a residual limb, with resilient-support between the residual tissue area and a bell-shaped support bracket.

The force-distribution support structure 10 can be assembled upon a support bracket 20. As shown in FIGS. 1A and 2, the support bracket 20 can be coupled to both a stem 60 at the proximal end 200 and a resilient-support 40 at the distal end 400. More specifically, the support bracket can be a framework by which a resilient-support can be operably attached to the stem and, thus, to the terminal bone end. This can allow the resilient-support to receive the forces of ambulation typically applied to the terminal bone end. In certain embodiments, the shape of the support bracket can also assist in providing a more normalized pattern of ambulation.

In one embodiment, shown, for example, in FIGS. 1A, 1B, 1C and 1D, the support bracket 20 has a generally bell-shaped housing 21 with a hollow interior 22 that can contain, at least partially, the resilient-support. In one embodiment, the bell-shaped housing has a generally hemispherical or semi-hemispherical shape. In an alternative embodiment, the bell-shaped housing is more oval in shape. In another alternative embodiment, the bell-shaped housing has a non-symmetrical shape. However, the shape of the bell-shaped housing can have any of a variety of configurations, ranging from, by way of non-limited examples, circular or oval to more square, rectangular, or even triangular in shape, or combinations thereof, which can be non-symmetrical.

Figure 1B:
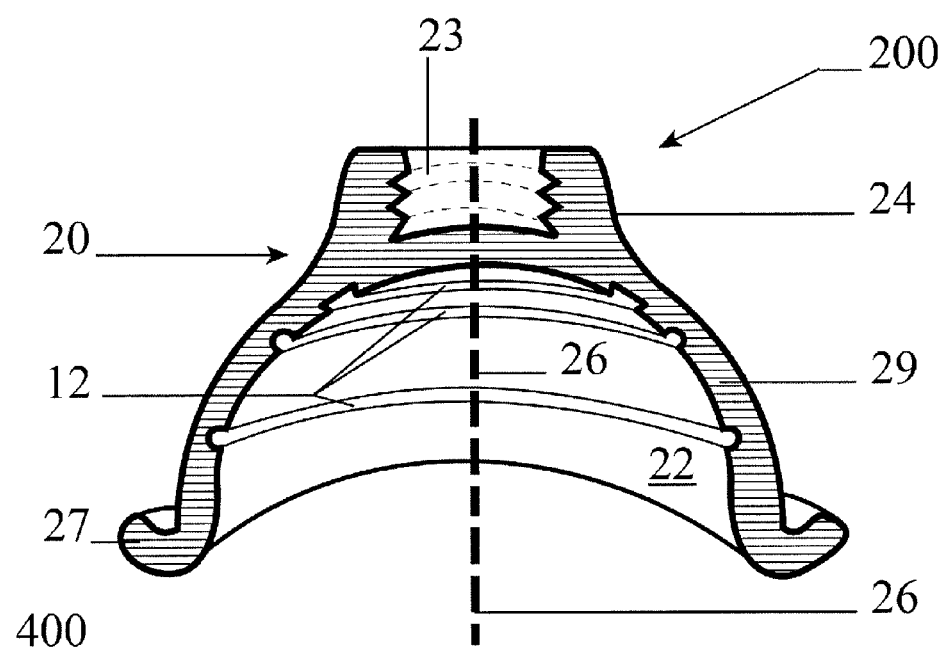
FIG. 1B is a cross-sectional view of one embodiment of a bell-shaped support bracket for a FDSS, according to the subject invention.
Figure 1C:
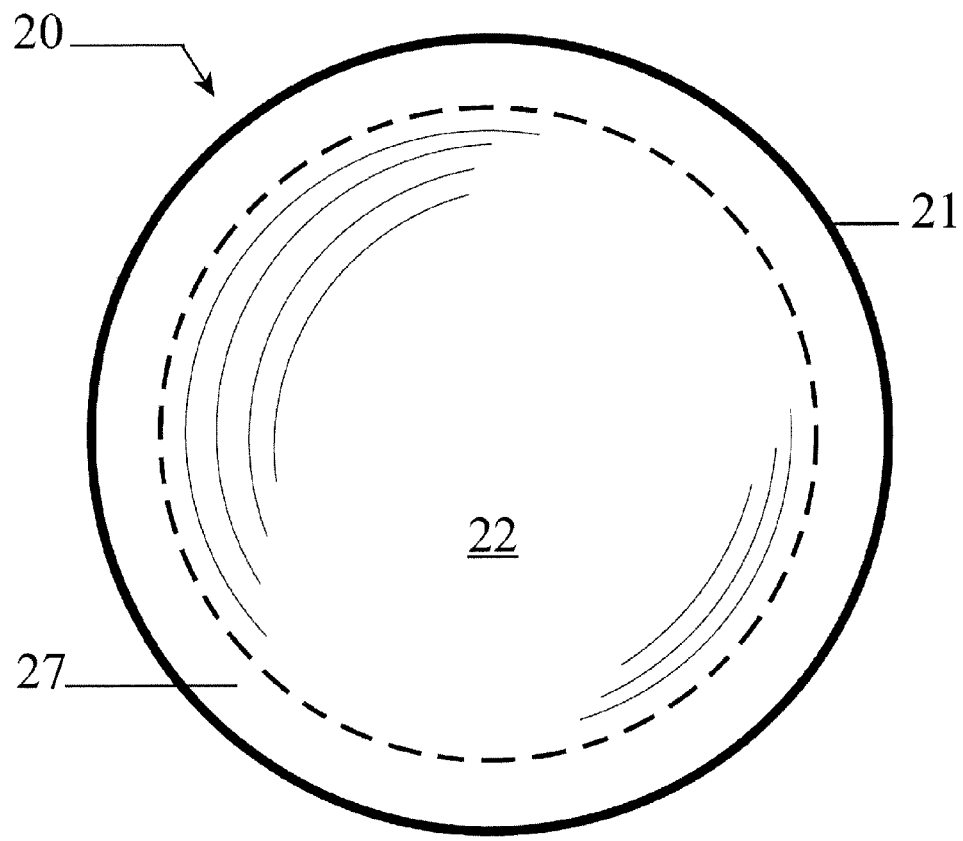
FIG. 1C is a bottom plan view of an embodiment of a bell-shaped support bracket for a FDSS, according to the subject invention.
Figure 1D:
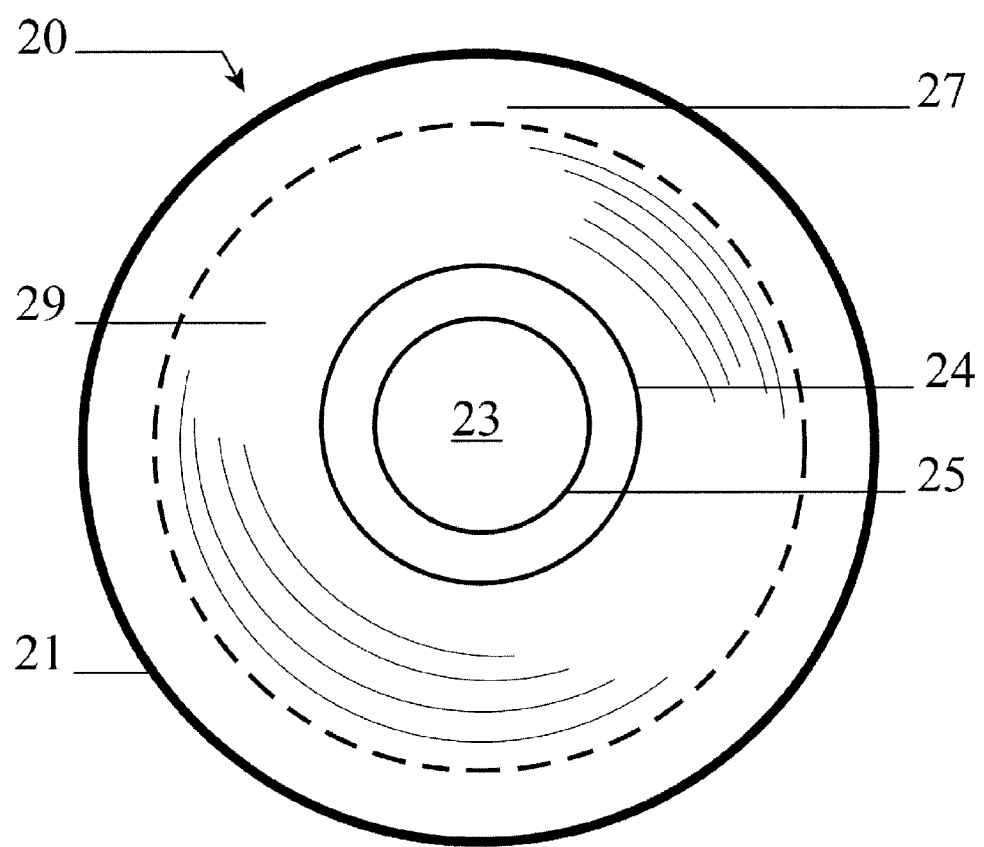
FIG. 1D is a top plan view of an embodiment of a bell-shaped support bracket for a FDSS, according to the subject invention.
Figure 1E:
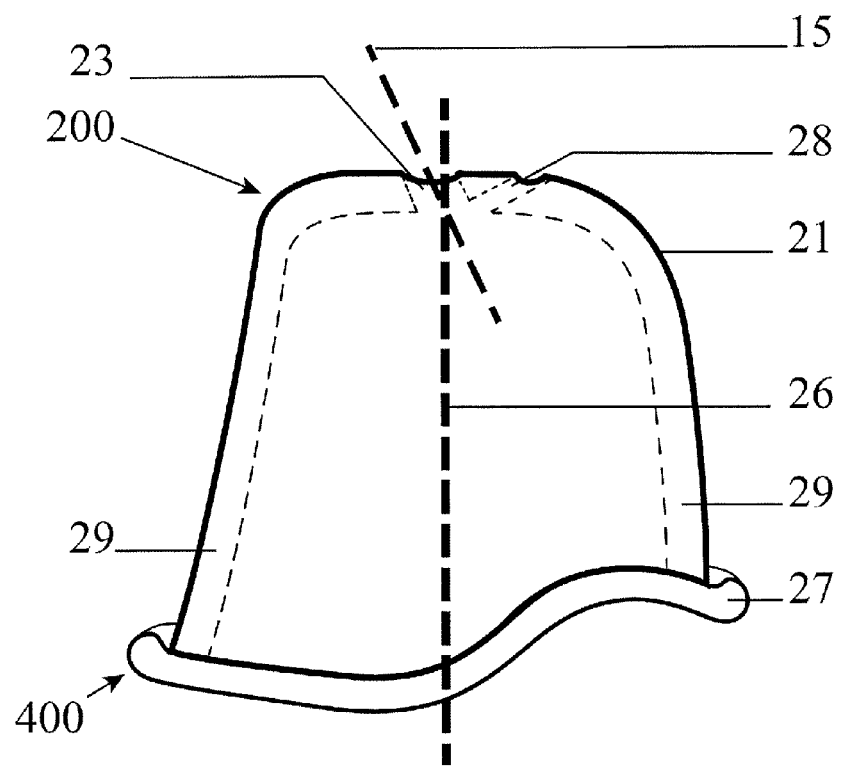
FIG. 1E is front plan view of an alternate embodiment of a bell-shaped support bracket for a force-distribution support structure (FDSS), according to the subject invention. Shown is a particular embodiment wherein the bell-shape is irregular and the bone is angled.

The hollow interior 22 can be uniform in shape, such that a lip 27 of the bell-shaped housing, which is that portion of the housing at or about the most distal end 400, is generally level or symmetrical, such as shown, for example, in FIGS. 1B and 1C, where the lip is level on all sides. In an alternative embodiment, the shape of the hollow interior 22 or the depth of the hollow interior, of the bell-shaped housing, is irregular or asymmetrical or is otherwise inconsistent from one side to another, such that the lip is not level on all sides. In one embodiment, the bell-shaped housing has an asymmetrical lip 27, with one or more sides that are higher than another side. In this embodiment, the lip 27 is curved or angled upwards or downwards, an example of which is shown in FIG. 1E.

The wall 29 of the bell-shaped housing can also be at least partially flat or have some curvature or some combination thereof. FIG. 1E illustrates an embodiment where one side of the bell-shaped housing wall 29 is more straight than the opposite side, which has a more pronounced curvature. Other embodiments can incorporate more or less curvature or have more of the wall with a flat shape. In one embodiment, the shape of the housing is indicative of the shape of the hollow interior 22. In an alternative embodiment, the shape of the housing does not reflect the shape of the hollow interior 22. Thus, the overall shape of a bell-shaped housing and the hollow interior can depend upon any of a variety of factors, such as, for example, the quality of the residual limb, the amount of resilient-support required, the size of the housing that can be utilized, and many other factors that are known to those with skill in the art. Such variations in the bell-shaped housing are considered to be within the scope of the present invention.

In another embodiment, the support bracket 20 comprises a generally saddle-shaped housing 30. In this embodiment, the saddle-shaped housing has a semi-tubular or U-shaped configuration, one example of which is shown in FIGS. 3A-E. The mounting support platform 31, at the proximal end 200 of this embodiment can be rounded, such that it has a convex-shaped surface, an example of which is shown in FIGS. 3C and 3D. Alternatively, the mounting support platform 31 can have a more planar surface.

In a further embodiment, the mounting support platform is contiguous with at least two sidewalls 32 that extend distally 400 from each side of the mounting support platform 31. The sidewalls and mounting support platform can create a partially tubular or U-shaped structure which also has a hollow interior 22 between a frontal end 250 and a caudal end 450, illustrated, for example, in FIGS. 3C, 3D, and 3E.

It can be observed that normal human ambulation usually entails a rocking motion caused by the weight of the body being shifted from the heels to the toes of alternate feet. While the prosthetic devices of the subject invention can restore the ability of the axial skeleton to manage the weight and force of ambulation, it can be further beneficial to restore, as much as possible, the normal walking motion. Therefore, embodiments of the subject invention can be configured, so that when utilized with an external prosthetic device, a more normal ambulation motion can be achieved.

Figure 3A:
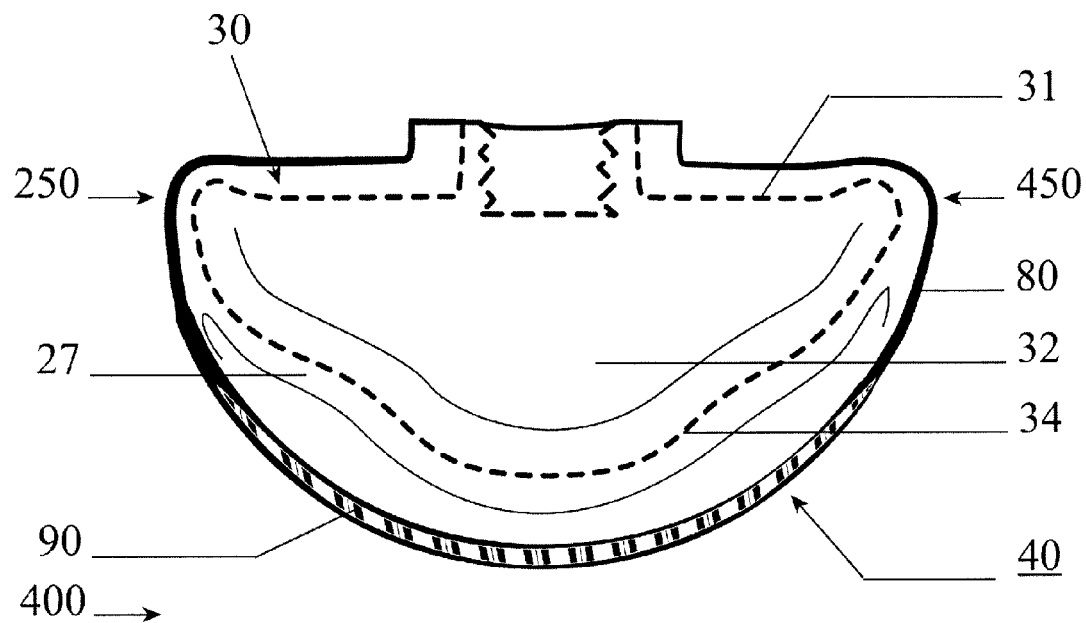
FIG. 3A is a right side elevation view of an embodiment of a FDSS with a saddle-shaped support bracket, according to the subject invention. In this embodiment, the support bracket is shown encased in a pliable, shock-absorbing sleeve.
Figure 3B:
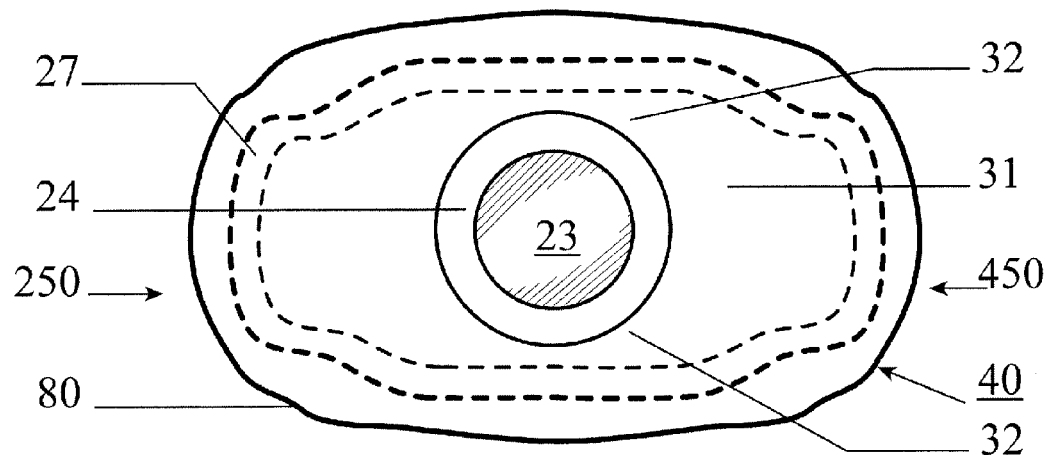
FIG. 3B is a top plan view of an embodiment of a FDSS with a saddle-shaped support bracket, according to the subject invention. In this embodiment, the FDSS is shown encased in a pliable, shock-absorbing sleeve, which surrounds a bore.
Figure 3C:
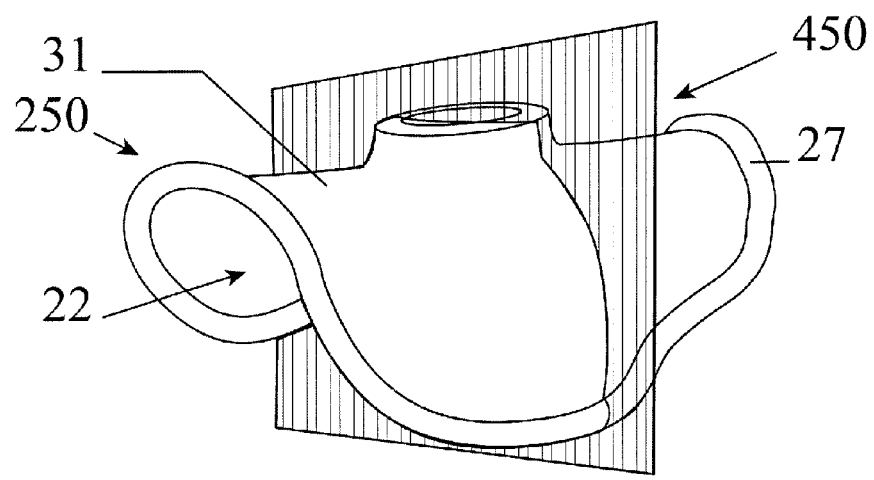
FIG. 3C is a right-side perspective view of an embodiment of a saddle-shaped support bracket. The lateral medial plane that bisects the bracket indicates the cross-section shown in FIG. 3D.

In one embodiment, the distal end 400 of the sidewalls 32 of a saddle-shaped bracket are curved, between the frontal end 250 and the caudal end 450, so that the distal ends of the sidewalls and lip 27 form a circular or semi-circular form, which is shown, by way of non-limiting example, in FIGS. 3A and 3C. This embodiment of a saddle-shaped bracket allows the sidewalls to mimic the shape of a normal bone joint and can provide a posterior-to-anterior rocking motion that mimics the natural "heel-to-toe" ambulation motion. When implanted into a residual limb, most or all of the ambulation force is first applied to the caudal end 450. As the weight of the body moves forward, the curved sidewalls of the bracket can cause the ambulation forces to move or "rock" towards the frontal end 250 of the bracket. This rocking of the ambulation forces from the caudal end to the frontal end allows the residual limb to mimic a more natural walking motion.

In an alternative embodiment, the sidewalls can have an irregularly curved distal end 400, where one or both of the side walls and the lip 27 form a multi-curvate shape. In one embodiment, the sidewalls can have one or more indentations 34 that create a multi-curvate distal end, such as shown, for example, in FIG. 3A. In a still further embodiment, the sidewall indentations are more pronounced, giving the sidewalls a more multi-curvate shape, such as shown, by way of example, in FIGS. 4A and 4B.

Still other alternative embodiments can have sidewalls that are less rounded and have sharper angles or straighter edges. Each sidewall 32 can also have a different shape or height. Thus, the saddle-shaped bracket housing could be customized for each amputee. These and other variations can be understood and devised by a person with skill in the art. Such variations, which function in substantially the same way and provide substantially the same result, are considered to be within the scope of the subject invention.

As will be discussed further below, the support bracket 20 can be operably attached to a resilient-support 40. When the entire force-distribution support structure (FDSS) 10 is implanted, such as shown, as a non-limiting example, in FIG. 2, the support bracket can exert forces against the resilient-support that are at least equivalent to the forces that would be exerted on a normal lower limb. The resilient-support, attached to the terminal bone end by the support bracket and stem can protect the residual tissue area. It is advisable for the material of the resilient-support to be not only be sufficiently pliable, but also capable of withstanding the compression forces that are expected to be exerted thereon. However, it can be beneficial if the structure of the support bracket is such that it minimizes or eliminates surfaces that have the potential to puncture, rupture, cut, score, abrade, or otherwise damage the resilient-support. It can be particularly beneficial, if the side walls and/or the lip 27 is configured so as to prevent damage or minimize wear on the resilient-support, since it will be these surfaces that often exert the most concentrated force against the resilient-support.

In one embodiment, the lip 27 of a support bracket has non-sharp edges or edges that are curved, rounded, beveled, bent, flared, widened, or otherwise shaped to reduce or eliminate sharp or rough edges in contact with a resilient-support. In one embodiment, a support bracket 20 terminates at the distal end 400 with a lip that is rounded or beveled, such as shown, for example, in FIG. 3D. In another embodiment, the lip 27 is curved outward from the hollow interior 22, such as shown, for example, in FIGS. 1A, 1B and 2. Alternatively, the lip can be curved inward or towards the hollow interior of a support bracket. The enlarged lip can present a generally smooth, finished edge with a larger surface area, such that when forced against a support, the lip inhibits or prevents a bracket 20 from causing damage to the support. The amount of curvature imparted to the lip can vary, but ideally would provide a surface area sufficient to adequately prevent damage to a resilient-support.

Figure 4A:
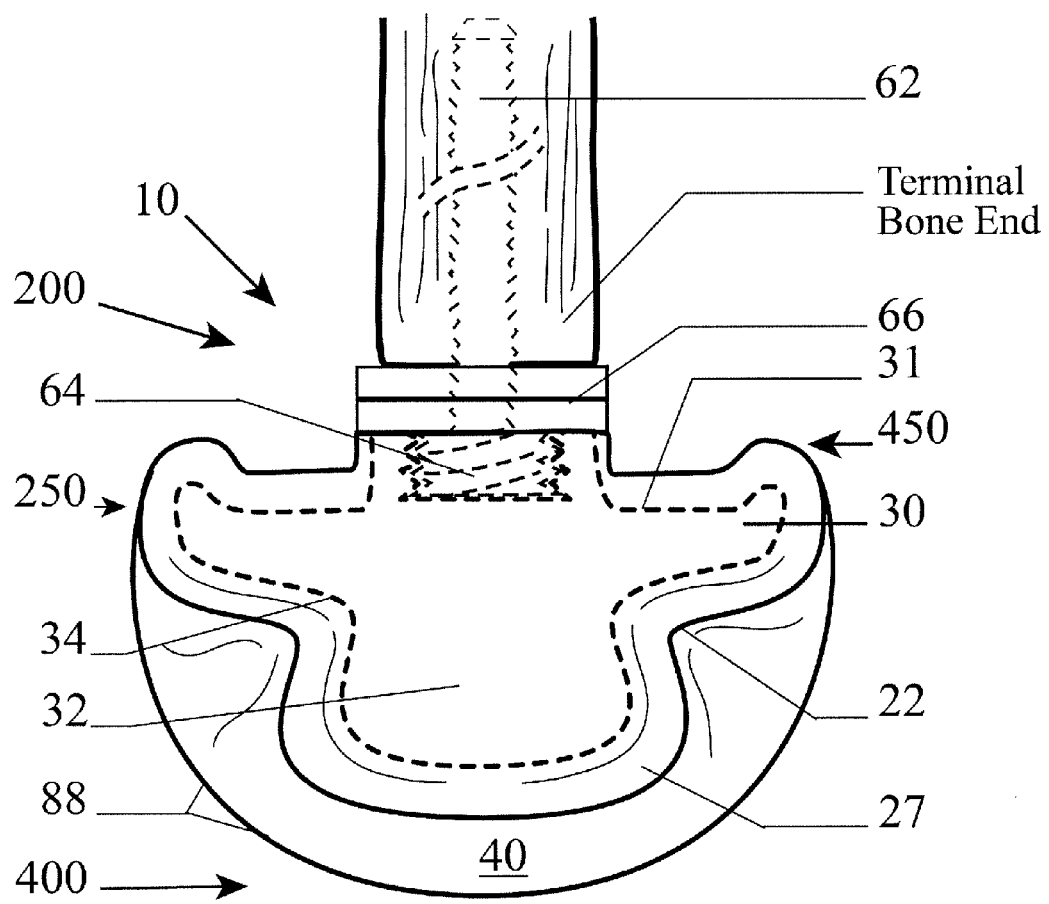
FIG. 4A is a right side elevation view of a FDSS having an alternative embodiment of a saddle-shaped support bracket, according to the subject invention, implanted onto the terminal bone end of a residual limb.
Figure 4B:
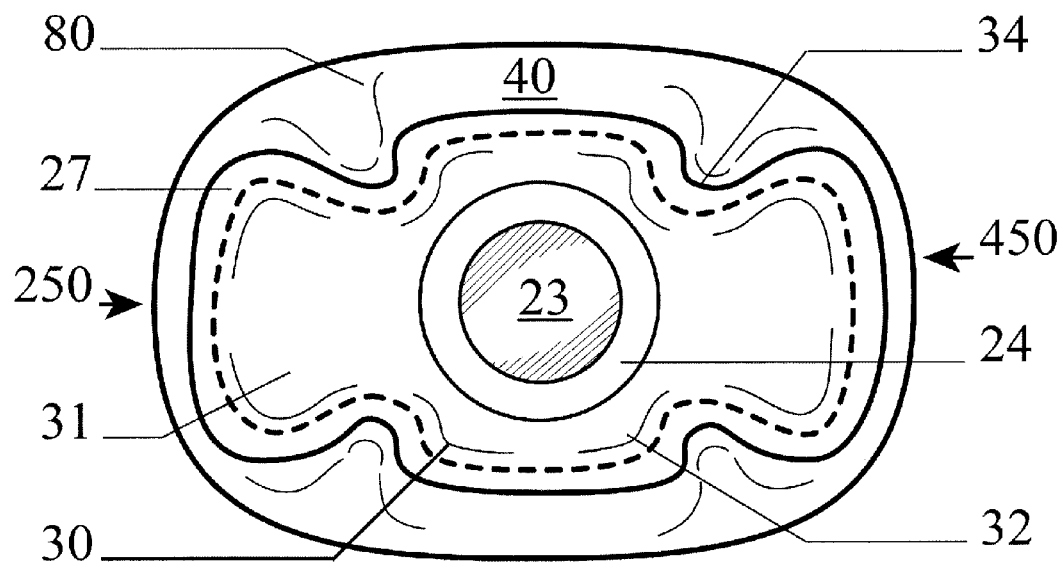
FIG. 4B is a top plan view of an FDSS having an alternative embodiment of a saddle-shaped support bracket with a resilient-support operably attached, according to the subject invention.
Figure 4C:
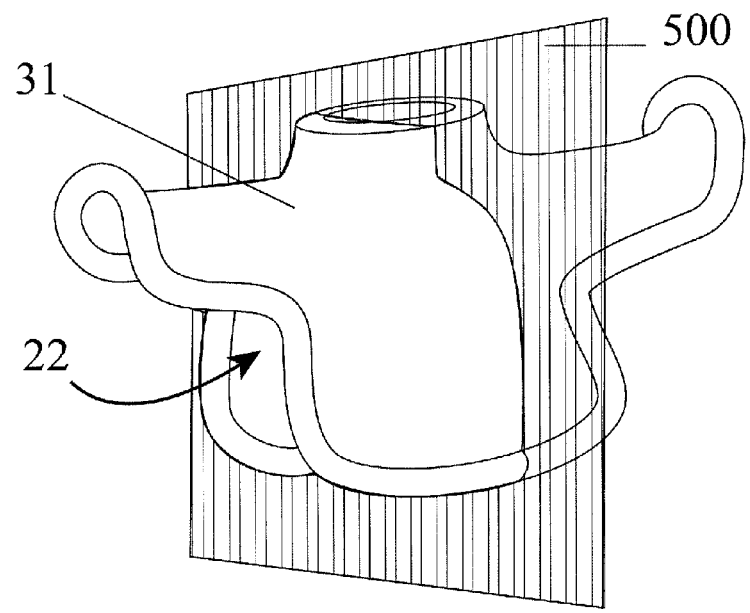
FIG. 4C is a right-side perspective view of an alternative embodiment of a saddle-shaped support bracket for a force-distribution support structure. The plane that bisects the bracket in this view indicates the cross-section shown in FIG. 4D.

In yet another embodiment, the lip 27 has a generally rounded circumferential shape as shown, by way of non-limiting example, in FIGS. 1E, 3C and 4C. A rounded circumferential shape also has the benefit of providing a larger surface area for distributing forces and can inhibit or prevent damage to the resilient-support. The circumferential shape can also be other than circular and can include one or more flat surfaces. The diameter of the circumferential shape can vary, but, ideally, would be large enough to adequately distribute forces and prevent damage to the resilient-support.

In a further embodiment, the wall 29 of a bell-shaped housing and the mounting support platform 31 and/or the sidewalls 32 therefrom can have a shape that inhibits damage to the resilient-support. In one embodiment, the housing and/or the sidewalls are flared outward from the hollow interior 22, such that the distal end 400 is wider than the proximal end 200. This flaring can inhibit forces, particularly downward forces, from being concentrated onto a single area of the resilient-support and allows a greater area of the housing and/or the sidewalls to assist in distributing forces over more of the resilient-support. FIGS. 1B and 3D illustrate examples of a support bracket housing and sidewalls that have a flared shape. Other embodiments can have a more or less flared shape.

In a further embodiment, particular to a saddle-shaped support bracket, the frontal end 250 and the caudal end 450 of the mounting support platform 31 can be flared upwards, or in the proximal direction. This upward flaring of the ends can provide the same advantage as flared sidewalls in that it can prevent forces, particularly downward forces, from being concentrated onto a single area of the resilient-support and allows more of the supporting bracket to assist in distributing forces over more area of the resilient-support.

In a still further embodiment, the lip, which can be modified as described above to reduce damage to the resilient-support by the side walls, extends over to the frontal end and caudal ends, an example of which is shown in FIGS. 3B, 3C, 4B, 4C and 4F. As described above, the lip can provide greater surface area and protection to the resilient-support.

The concept of distributing forces over a larger surface area by modifying such surfaces is known in the art. Thus, other types of lip shapes, housing, or sidewall configurations that inhibit damage to a resilient-support, according to the subject invention, can also be used separately or in addition to the above-described embodiments. It would be within the skill of a person trained in the art to devise any of a number of ways to modify a support bracket and/or the lip for such a reason. Such modifications, which are not inconsistent with, and provide substantially the same results as, the teachings herein, are within the scope of the present invention.

The support bracket embodiments of the subject invention act as a framework to which a resilient-support 40 can be operably attached and ultimately affixed to a terminal bone end. The resilient-support is a mechanism by which the forces of ambulation are absorbed and distributed to alleviate pressure and pain on the amputated limb. As such, attachment of the resilient-support to the support bracket should be secure, stable, and capable of withstanding forces of ambulation. To facilitate such attachment, the support bracket can have any of a variety of structures or features that can cooperatively engage with or otherwise form some further complimentary attachment to, or with, a resilient-support.

Figure 3E:
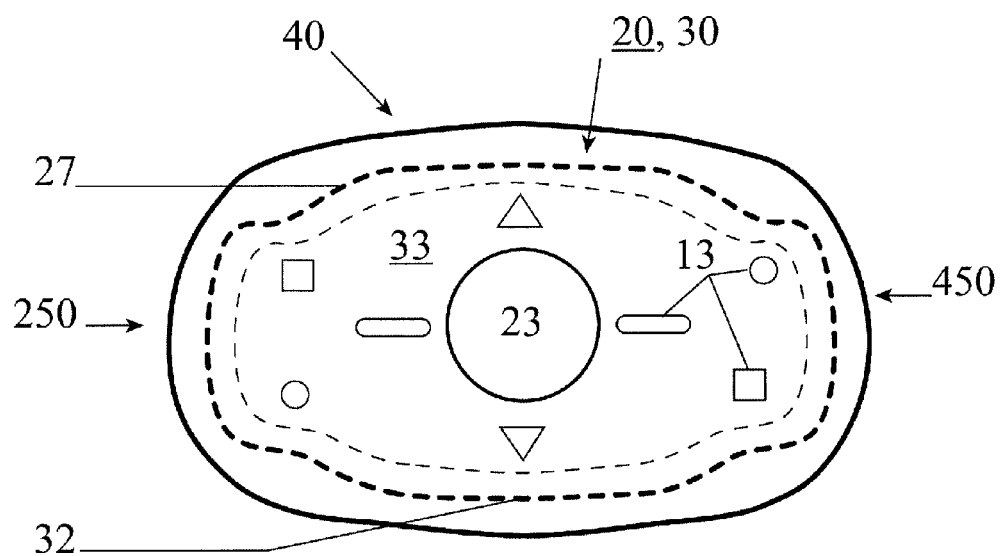
FIG. 3E is a bottom plan view of an embodiment of a saddle-shaped support bracket for a force-distribution support structure (FDSS), according to the subject invention. In this embodiment, the FDSS is shown encased in a pliable, shock-absorbing sleeve.
Figure 3D:
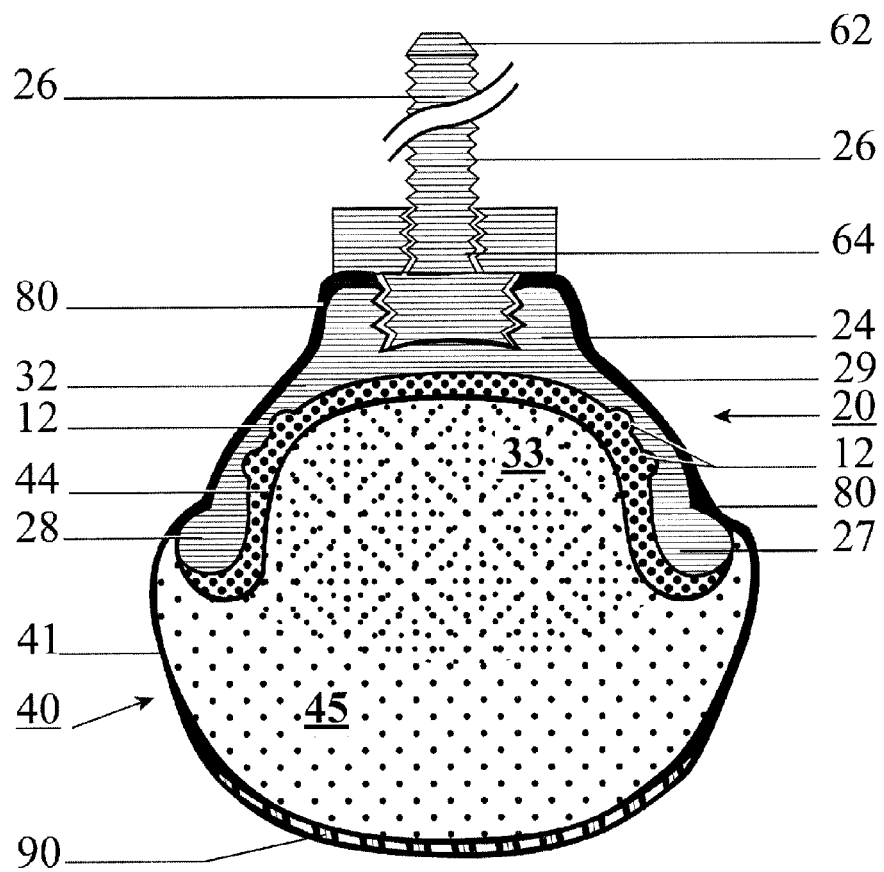
FIG. 3D is a cross-sectional view, along the lateral medial plane shown in FIG. 3C, of an embodiment of a FDSS having a saddle-shaped support bracket, according to the subject invention.
Figure 4D:
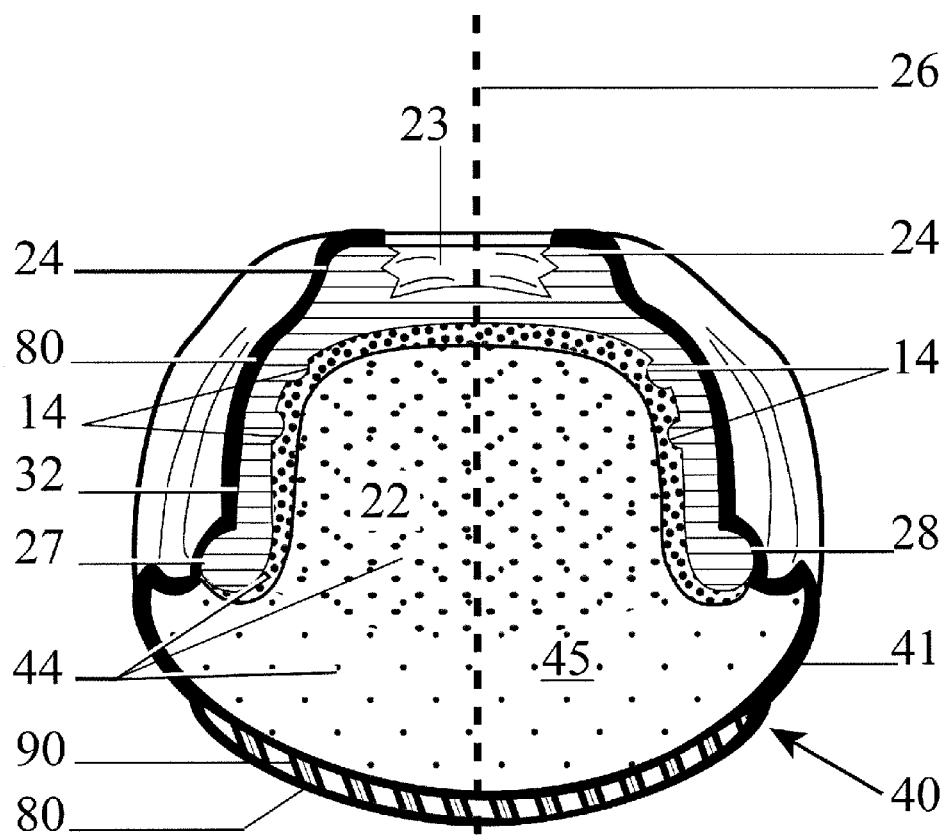
FIG. 4D is a cross-sectional view, along the lateral plane shown in FIG. 4C, of an embodiment of a force-distribution support structure having an alternative embodiment of a saddle-shaped support bracket, according to the subject invention.
Figure 4E:
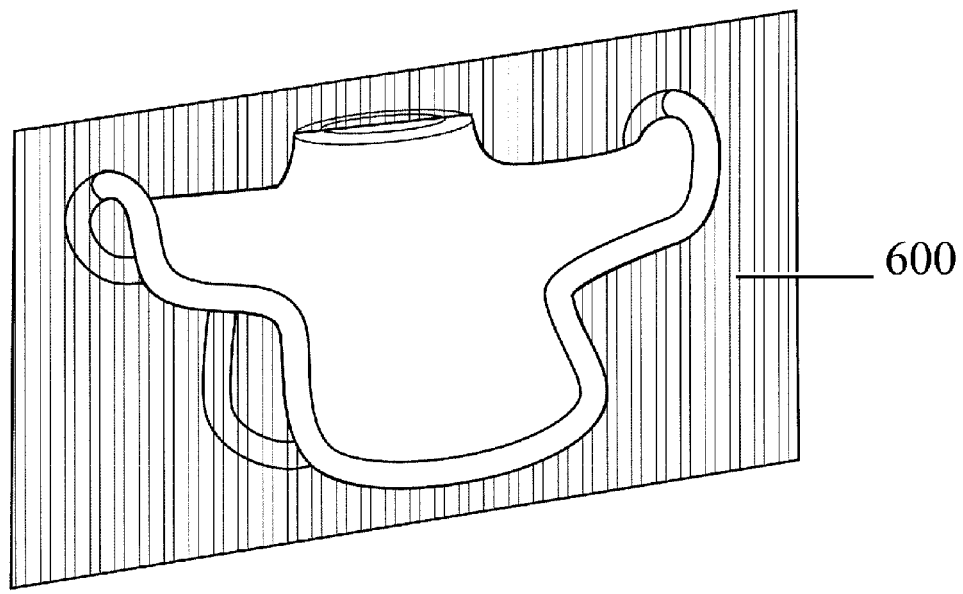
FIG. 4E is a right-side perspective view of an alternative embodiment of a saddle-shaped support bracket for a force-distribution support structure. The median sagittal plane that bisects the bracket in this view indicates the cross-section shown in FIG. 4F.
Figure 4F:
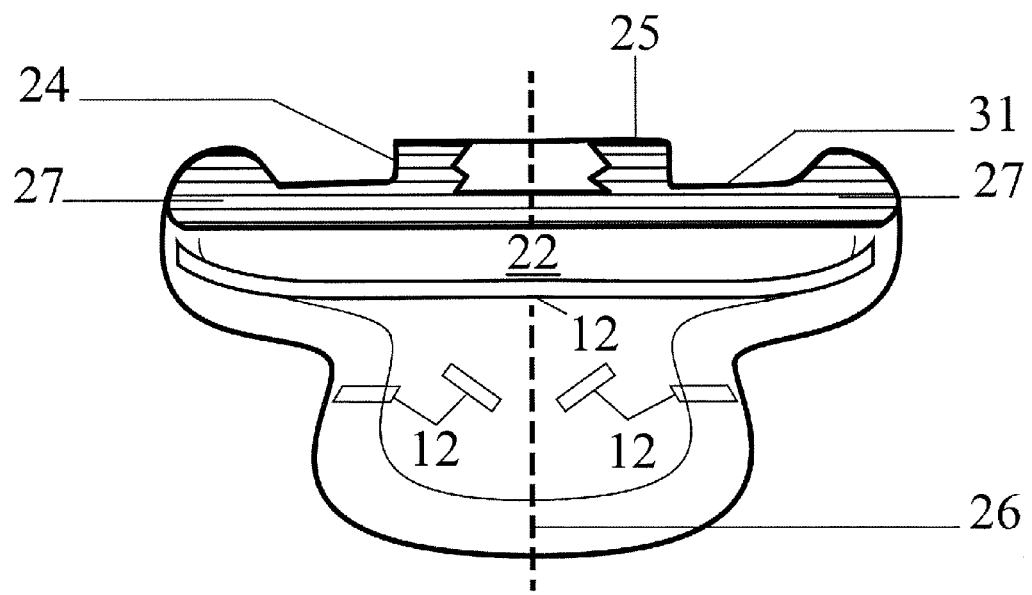
FIG. 4F is cross-sectional view, along the median sagittal plane shown in FIG. 4E, of an alternative embodiment of a saddle-shaped support bracket, according to the subject invention. Also shown is an alternative embodiment having grooves within the housing.

In one embodiment, a support bracket has one or more grooves 12 forming one or more ingresses within the housing for receiving the material of a resilient-support. The grooves 12 and material can form a sort of tab-and-slot configuration that can hold the material of the resilient-support in place. In one embodiment, the grooves are within the housing of a support bracket. More specifically, a hollow interior 22 of a support bracket can have one or more grooves 12. The grooves 12 can extend in any direction or at any angle that is efficacious for attachment of the support. Ideally, the material (s) of the resilient-support will operably connect with, or otherwise conform to, the shape of the groove, forming an anchoring structure to inhibit removal of the resilient-support from the support bracket. FIG. 1B illustrates an embodiment of a bell-shaped housing having grooves within the hollow interior 22. FIGS. 3D and 4F illustrate embodiments of a saddle-shaped housing having alternative embodiments of grooves within the hollow interior 22.

In one embodiment, the grooves are formed as a continuous channel, as shown in the embodiments in FIGS. 1B, 3D and 4F. Alternatively, the grooves can be discontinuous or variable in length, as shown for example in FIG. 4F. Further, the grooves can be generally perpendicular with a center line 26 of the support bracket, such as shown, for example, in FIG. 1B. Alternatively, the grooves can be angled or curved so that they are not generally perpendicular with the center line, also as shown in an example in FIG. 4F. However, since the purpose of the grooves is to inhibit a resilient-support from disengaging with a support bracket, it can be beneficial if the one or more grooves are positioned so as to prevent movement of the conforming material or sliding of the conforming material away from the support bracket.

In an alternative embodiment, a support bracket has one or a plurality of orifices 13 arranged within the housing that can engage with the material of a resilient-support. The orifices can have any of a variety of shapes or configures, including, but not limited to, circular, oval, square, triangular, oblong, or any other polygonal shape. FIG. 3E illustrates an embodiment of a support bracket having multiple orifices 13 within the hollow interior 22 of the housing. As with the grooves, described above, the orifices allow the material of the resilient-support to conform to the shape of the orifice to assist in operably connecting the support bracket and the resilient-support.

In a still further alternative embodiment, a housing has one or a plurality of protrusions 14 extending therefrom around which the material of a resilient-support can conform. In one embodiment, within the hollow interior of a housing there are a plurality of ribs, nubs, or other types of raised areas that the material of the resilient-support can conform to or around. FIG. 4D is a cross-sectional view taken along the lateral median plane 500 shown in FIG. 4C, illustrating one example of this embodiment. Protrusions 14 can take any shape or form that will assist in securing a resilient-support to a support bracket without causing damage when forces are applied to the resilient-support.

The materials that can be utilized for a support bracket are preferably non-reactive and/or biocompatible materials capable of long-term in vivo use. Such materials can include, by way of non-limiting examples, various types of metals, metal alloys, plastics, glass, ceramics, naturally-derived products, or combinations thereof. More specific examples can include, but are not limited to, titanium, cobalt-chromium-molybdenum alloy, steel, titanium-carbide-coated stainless steel, nylons, polyethylenes, hydroxyapatite (phosphocalcic ceramic), bone fusion matrix materials, or combinations of these or other materials that are suitable for in vivo use. The selection of an appropriate non-reactive and/or biocompatible material is within the competence of those skilled in the art. It should be understood that variations in material, which perform the same function, in substantially the same way, with substantially the same result, are within the scope of the subject invention.

For implantation, the support bracket is typically operably connected at or about, the terminal bone end within a residual limb. There are any of a variety of devices and associated techniques currently available for attaching devices to the intramedullary bone space or the extramedullary bone, or some combination thereof. For example, any of a variety of anchoring screws 5 can be used to affix a structure to a bone. However, most types of anchoring devices and materials are typically ill-suited for direct in-line attachment to the terminal end of a bone. Ideally, a device for terminal bone end attachment can provide a stable fixation of the FDSS without damage to the remaining bone end either during installation or during later use by an amputee. It can also be beneficial if such attachment devices permit bone ingrowth as a means of further stabilizing the structure.

One embodiment of the subject invention utilizes an elongated stem 60 to operably connect the support bracket to the bone end. In one embodiment, the stem has a first end 62 that can be introduced into the intramedullary bone space and an opposite second end 64 that can be connected to an embodiment of a support bracket of the subject invention. The first end can be introduced into the intramedullary bone space from the terminal, or severed, bone end. The second end can be attached to a support bracket having one or more structures or features for receiving the second end. Such attachment to the support bracket can be permanent, which for some amputees may be preferred. However, one advantage of the embodiments of the subject invention is the modularity that can be provided to the FDSS 10. Modularity of the components allows them to be changed, modified, repaired, replaced, or even eliminated if necessary. To achieve this modularity, the stem and the support bracket can be configured with a removable or non-permanent connection.

In one embodiment, the stem is a generally elongated rod-like device. In one embodiment, the first end of the stem is advanced into a terminal bone end. This can be achieved by first drilling, tapping, or otherwise creating a channel into the intramedullary bone space, from the terminal end. The first end 62 can then be advanced into the intramedullary bone space through the channel. Once the first end is in place within the bone, one or more anchoring structures can also be used to secure the first end within the bone. By way of non-limiting example, one or more anchoring screws 5 can be laterally placed through the bone to secure the first end, an example of which is shown in FIG. 2.

Alternatively, the first end can be fixedly attached to the terminal bone end with little or no contact with the intramedullary bone space. In one embodiment, the first end has a shape conducive to being secured to the extramedullary bone. In one embodiment, the first end can be secured to the extramedullary bone surface with one or more brackets, plates, braces, or similar devices. It would be within the skill of person trained in the art to determine any of a variety of devices and techniques that can be used to fixedly attach a first end to a bone in a residual limb. It should be understood that such alternatives are within the scope of the subject invention.

Figure 5A:
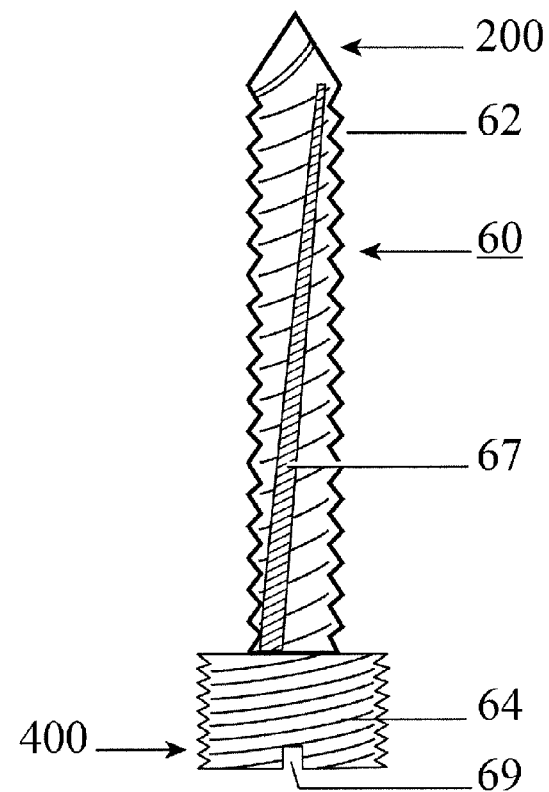
FIG. 5A is a front plan view of one embodiment of a stem, according to the subject invention, for securing a FDSS to a terminal bone end.

In a specific embodiment, a stem 60 is configured similarly to a headless screw and is utilized to removably and operably connect a support bracket 20 to the terminal bone end. This embodiment has a first end 62 that is configured with continuous threading that is conducive to attachment within the intramedullary bone space. In a further embodiment, the first end is a self-tapping or thread-cutting screw, such that when advanced into the intramedullary bone space, the continuous male threads on the first end 62 cut the tissue within the intramedullary space to create complementary continuous female threads. FIG. 5A illustrates a non-limiting example of this embodiment. In a further embodiment, the first end has at least one flute 67 extending from, at or about, the proximal end 200 to, at or about, the distal end 400 of the first end 62. The flute provides a channel by which excess material from the intramedullary bone space can exit, as the first end advances into the bone space. In one embodiment, the flute is cut in a generally straight line along the length first end. In an alternative embodiment, the flute is cut as a spiral that winds, at least partially, around the circumference of the first end. FIG. 5A further illustrates one example of a fluted first end embodiment.

Ideally, the living bone in the residual limb will form a permanent, or at least semi-permanent, attachment to the first end 62. Such bone ingrowth is not uncommon and can be beneficial. It not only secures the first end, but can increase the strength of the bone. In a further embodiment, the first end of a stem 60 is configured with multiple indentations or holes 63 that encourage deeper bone ingrowth. In a still further embodiment, the first end 62 is configured with one or more hollow chambers 68 therein that are contiguous with the holes 63. A chamber 68 allows bone ingrowth into the holes 63 to extend into the chamber 68 forming a permanent attachment of the first end to the terminal bone end. However, the modularity of the embodiments of the subject invention provides the ability to modify, repair, or replace components without removal of the stem from the bone, in most situations. Thus, the increased bone ingrowth can be advantageous in most circumstances.

The second end 64 of the stem 60 can have a permanent or removable operable attachment to a support bracket. The attachment of the second end to the support bracket secures the resilient-support, attached thereto, to the terminal bone end. The operable attachment of the second end 64 to the support bracket can be accomplished by any of a number of devices and techniques known to those with skill in the art. In one embodiment, attachment of the second end can be achieved by utilizing one or more secondary devices, such as, for example, screws, pins, dowels, brackets, nuts and bolts, or other types of devices that attach to both the second end and the support bracket. In a specific embodiment, the second end is secured to the support bracket with one or more machine screws. In an alternative embodiment, the second end 64 can be affixed to the support bracket with adhesive, cement, or by soldering, chemical welding, or other more permanent method. While this would not be an ideal fixation method, as it inhibits or prevents modularity of the device, it can be an option if desired. It would be within the skill of a person trained in the art to determine any of a variety of secondary devices that can be used to secure a stem to a bone or to a support bracket. Such variations, which perform the same function, in substantially the same way, with substantially the same result, are considered to be within the scope of the subject invention.

Figure 5B:
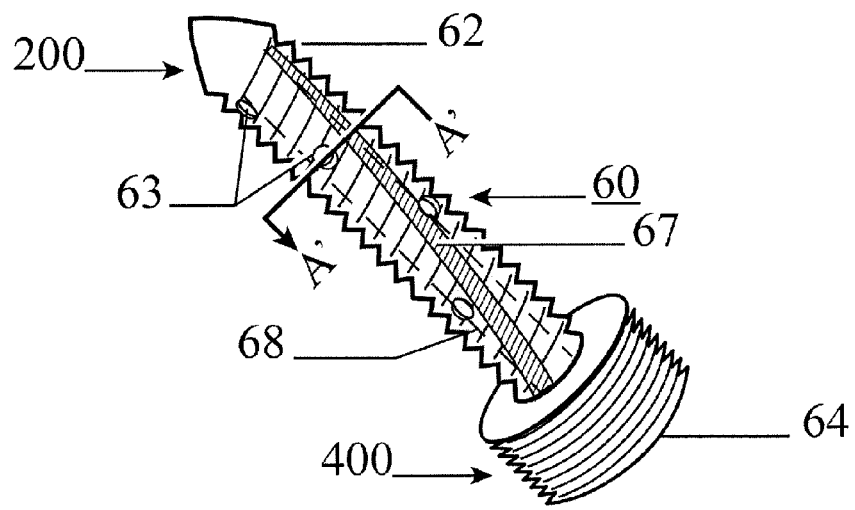
FIG. 5B is a right side perspective view of an alternate embodiment of a stem, according to the subject invention. Shown in this view are bone in-growth ports and a hollow chamber within the first end.
Figure 5C:
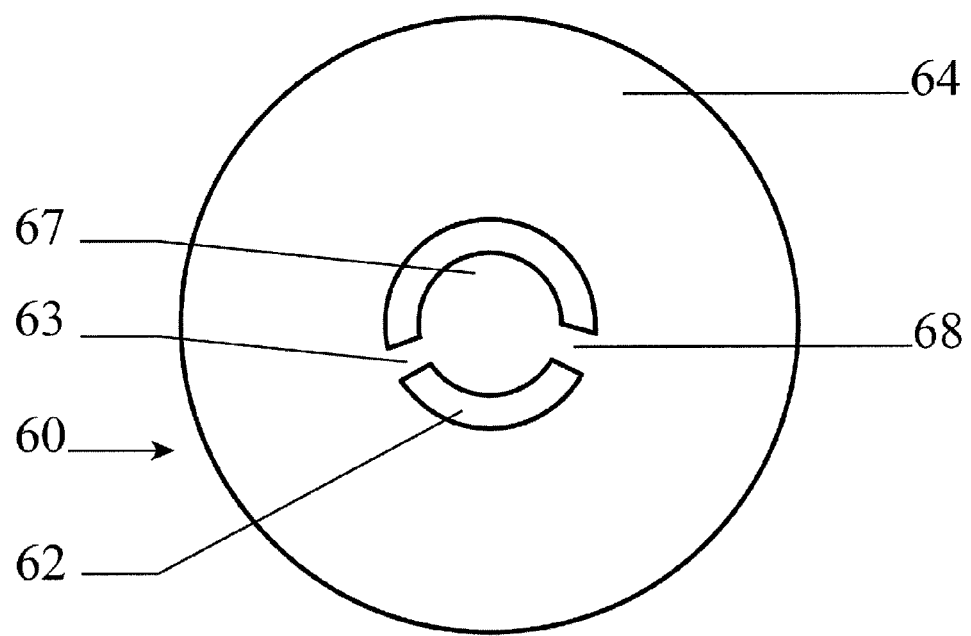
FIG. 5C is a top plan cross-sectional view of the embodiment of a stem, taken along line A'-A', as shown in FIG. 5B.

In a particular embodiment, the second end 64 of the stem is configured with continuous threading that is conducive to attachment to a compatible continuous in a threading support bracket. In a more specific embodiment, the stem is configured with machine-grade continuous threading compatible with machine-grade continuous threading within a support bracket. Machine-grade threads are typically a finer grade than other types of threading, having a low tolerance threshold between the male and female threads. This can be beneficial for inhibiting bone and/or tissue in-growth around the threading. In a further embodiment, the machine threads can be treated or covered with a substance that further inhibits bone and/or tissue in-growth. This embodiment provides advantageous modularity to the device, such that the support bracket can be removed for repair, alteration, and/or replacement, if necessary, without disturbing the placement of the stem. FIGS. 5A and 5B illustrate an embodiment of a stem having a machine threaded second end. FIGS. 1A and 3D illustrate an example of how a threaded second end can be operably connected to compatible threading in a support bracket.

While not required, it can be preferable for the stem to be milled as a single or unitary piece, where the first and second ends are a single material piece. However, it is possible for the first and second ends to be milled as separate pieces that are joined together. This would allow the first and second ends to be milled from different materials, if desired. The diameters of the first end 62 and the second end 64 of a stem 60 can vary and, further, each end, 62 and 64, can have the same or different diameters. The diameter required for any installation of an embodiment of the subject invention will depend upon factors known to those with skill in the art. For example, the length and diameter of the terminal bone end, as well as the quality of the terminal bone end can affect both the length and diameter required for installation of a first end 62. Further, the factors that can affect the length and diameter of a second end would also be understood by those with skill in the art. Such factors can include, by way of example, the type of support bracket embodiment utilized, materials utilized for the stem and/or the bracket, and the length and/or the diameter of the terminal bone end, and other factors known to those with skill in the art. In one embodiment, the diameters of the first end 62 and the second end 64 are equivalent or approximately equivalent. In an alternative embodiment, the diameter of the second end 64 is larger than the diameter of the first end 62, which is shown, by way of non-limiting example, in FIGS. 5A and 5B. In one embodiment, the length of the first end 62 is greater than the length of the second end 64. In an alternative embodiment, the length of the first end 62 is approximately equivalent to the length of the second end 64. In a still further alternate embodiment, the length of the second end is greater than the length of the first end.

Installation of the stem can be most easily accomplished by first fixing the first end to the terminal bone end, ideally into the intramedullary bone space. For easier installation, it can be efficacious for the first end 62 and the second end 64 to be previously attached, as described above. If the intramedullary bone space is drilled or cored prior to fixation, then it may be possible to insert or screw in the first end by hand. With the embodiments of the invention that are self-tapping or thread-cutting, it may be necessary to apply significant force to advance the first end into the intramedullary bone space. Often, a tool such as a screwdriver, wrench, drill, or similar device, either hand-held or motorized, can be used to install the first end. Thus, the second end of the stem can have one or more features or structures that accommodate attachment of a drill or similar device.

In one embodiment, the distal end 400 of the second end 64 of the stem 60 is modified as a screw head 69. In a specific embodiment, the second end is configured with a slot-shaped cut, cross-shaped cut, or other specially shaped opening (e.g., hex) formed therein to fit a tool, such as, for example, a screwdriver, hex wrench, drill driver bit, or similar device. In an alternative embodiment, the second end is configured with more than one type of screw head, such that it can accommodate more than one type of tool. By way of non-limiting example, a screw head 69 could have a modified cross-shaped cut that can work with both a straight-head and a cross-head tool. There could additionally be a hex-shaped opening to accommodate a drill bit or hex wrench.

If the first end and the second end are not pre-attached prior to installation, then it may be necessary for the distal end of the first end also to be modified as a screw head 69, as described above. In one embodiment, the distal ends of both the first end and the second ends of the stem are modified as screw heads. With this embodiment, the first end can be affixed to the terminal bone end and the second end of the stem can be affixed to the distal end of the second end.

It should be understood that the stem can be modified in any number of ways to accommodate use of a tool therewith. It would be within the skill of a person trained in the art to determine an appropriate modification for the particular application to which the embodiments of the subject invention will be applied. Thus, the use of a screw head configuration other than those described herein, which functions in substantially the same manner, performing the same function, to substantially the same result, is considered to be within the scope of the subject invention.

After the first end of the stem has been appropriately affixed to the terminal bone end, the second end 64 of the stem can be attached to a support bracket 20. It is possible for the second end and a support bracket to be attached prior to the first end being affixed to a terminal bone end. Such installation may be more difficult, though possibly preferable in certain situations.

The attachment of the second end to a support bracket can be achieved by several methods that can be either permanent or, in exemplary embodiments, allow removal of the support bracket. In one embodiment, at or about the proximal end 200 of a support bracket housing, there can be a bore 23 capable of receiving the second end 64 of a stem 60. In one embodiment, the bore opens at or about the proximal end of a support bracket 20 and is generally flush with the housing 21, as shown, for example, in FIG. 1E. The bore can also be continuous with a hollow interior 22, also shown, by way of non-limiting example, in FIG. 1E. Alternatively, the bore is not continuous with a hollow interior, as shown, by way of further non-limiting example, in FIG. 3D. In one embodiment, the second end 64 of the stem 60 can fit into the bore so that the proximal end of the second end 64 is substantially flush with the housing 21. This can allow the terminal bone end, affixed to the first end 62, to have contact with the housing or be at least in the proximity of the housing area around the bore.

In an alternative embodiment, there can be a neck 24 extending from at or about the proximal end of the housing. In this embodiment, the bore 23 is formed within the neck. In one embodiment, the bore traverses and is contiguous with the hollow interior 22 of a support bracket. In an alternative embodiment, the bore is not contiguous with the hollow interior 22 of a support bracket, an example of which is shown in FIGS. 1B and 3D.

In one embodiment, a terminal bone end, when engaged with a force-distribution support structure of the subject invention, would abut against the proximal end 200 of the neck 24, or at least be in closer proximity to the neck than to the housing. Examples of this embodiment are shown in FIGS. 1A, 2, and 4A. In an alternative embodiment, the neck has a diameter that allows a terminal bone end to extend over the neck and have contact with, or at least be in closer proximity to, the housing. In this embodiment, a terminal bone end can be prepared or altered so that the neck can extend fully, or at least partially, into the intramedullary bone space.

Depending upon the type of stem used, the bore and/or the neck can be configured with various structures or components for securing the stem therein. In one embodiment, the support bracket comprises one or more generally lateral holes 28 for receiving anchoring screws 5 to secure the stem within the bore. FIG. 1E illustrates one embodiment wherein a lateral hole within the housing can receive an anchoring screw to secure a second end of a stem within a bore 23. In an alternative embodiment, the neck 24 comprises one or more lateral holes 28 for receiving anchoring screws to secure the stem in the bore. FIG. 2 illustrates an embodiment having a lateral hole within a neck for receiving an anchoring screw to securing a second end of a stem within the bore in the neck. In a further embodiment, the second end of the stem can be configured to cooperatively engage with one or more anchoring screws 5, such as for example, machine screws, to prevent release of the second end from the bore once a stem is in place. The modifications that can be made to the second end for cooperatively engaging with a screw can include, but are not limited to, holes, cut-outs, channels, ducts, notches, and similar indentations within a second end of a stem into which the screw S5 can be engaged. Alternatively, a second end can be modified with, by way of non-limiting example, various types of ridges, extensions, protrusions, shelves, dimples, shoulders, or similar extensions thereon that prevent a stem from exiting a bore once an anchoring screw is engaged therewith. It is within the skill of a person trained in the art to devise any of a variety of techniques and devices for securing a stem within a bore. Such variations are considered to be within the scope of the subject invention.

In a specific embodiment, that can be particularly useful with a headless screw, the bore 23 comprises continuous threading that is compatible with continuous threading on the second end 64 of the stem. In a more specific embodiment, the bore comprises continuous machine threading that is compatible with continuous machine threads on the second end of a stem. FIGS. 1A, 1B, 2, 3D, and 4A illustrate examples of this embodiment. To secure the support bracket to the stem, the second end of the stem can be screwed into the bore. If necessary, additional holes 28 and anchoring screws 5, as described above, can be used to prevent the threaded stem from unscrewing from the bore 23.

When a FDSS is installed onto a terminal bone end, the position of the housing may need to be adjusted for each patient. Once the correct angle, direction, tilt, and other positional factors have been optimized, the housing can be secured in that position. This case can be facilitated by the use of one or more anchoring screws 5. In one embodiment, the FDSS is adjusted by altering the attachment of the stem to the terminal bone end. With this embodiment, one or more anchoring screws can be employed to fix the position of the stem relative to the terminal bone end, in a desired position as described above. In another embodiment, the FDSS is adjusted by altering the attachment of the support bracket to the stem. With this embodiment, one or more anchoring screws can be employed to fix the position of the support bracket relative to the stem, also as described above. In still another embodiment, both the attachment of the stem to the terminal bone end and the attachment of the support bracket to the stem can be adjusted to obtain the optimum position of the FDSS. With this embodiment, one or more anchoring screws can be utilized to secure the stem relative to the bone and to secure the support bracket relative to the stem in desired positions.

Advantageously, these embodiments can provide modularity to the device, such that the support bracket and resilient-support 40 can be removed from second end 64 of a stem, without disturbing the placement of the first end 62 of the stem with the terminal bone end. Thus, if the force distribution support structure 10 has been installed for a sufficient time that bone ingrowth has occurred, the support bracket and resilient-support can be removed, if necessary or desired, while leaving the securely held stem in place within the bone.

Usually, when a support bracket is installed, the terminal bone end can abut against the housing of a support bracket 20. If the support bracket has a neck 24, then the terminal bone end can abut against the proximal end 200 of the neck. Obviously, there can be significant variation in the shape, diameter, and/or quality of a terminal bone end between amputees, which can present some difficulty if a particular terminal bone end is not compatible with the dimensions of an available support bracket. Therefore, it is to be understood that a support bracket can be modified to accommodate various terminal bone ends.

The factors that can be considered by those skilled in the art with regard to the choice of materials for components of the subject invention have been discussed above with regard to the support bracket and are reasserted here with regard to the stem. Ideally, the materials utilized for a stem are preferably non-reactive and/or biocompatible materials capable of long-term in vivo use.

Another affliction that amputees often must contend with is abduction of a residual limb. Abduction is the tendency of the femur to move outward from the median sagittal plane of the body. Under normal circumstances, the legs maintain alignment with the median sagittal plane of the body because of the connection of the femur with the lower leg through the knee. Proper alignment provides the body posture necessary for normal ambulation. Obviously, an amputee that has lost a lower leg and possibly the knee joint no longer has this natural alignment mechanism. When a prosthetic device is attached to a residual limb, it is usually aligned with the remaining femur so as to provide a more natural gait. However, in the absence of a knee, the remaining muscles, or portions thereof, within the residual limb, hip, and lower body are required to more actively maintain alignment of the residual limb with the prosthetic device. If the remaining muscles are unable to maintain the alignment, the residual limb tends to bow outward, i.e., abduct away from the median sagittal plane, causing an unnatural, usually uncomfortable, and potentially structurally damaging gait. Fortunately, embodiments of the subject invention can be configured to compensate for or control abduction of a residual limb.

The embodiments of the subject invention can be installed so that they align with a sagittal plane 600 of the body (i.e., an anterior-posterior plane, as shown, for example, in FIG. 4C). By way of non-limiting example, a force-distribution support structure having a bell-shaped housing can be installed so that the center axis 26 of the housing is substantially aligned with the sagittal plane 600 of an amputee. By way of another non-limiting example, a force-distribution support structure having a saddle-shaped housing can be installed so that the hollow interior 22 is substantially parallel with a sagittal plane of the body.

In one embodiment, the housing 21 and the bore 23 are aligned, such that the bore is generally coaxial with the central axis 26 of a support bracket 20 of a force-distribution support structure 10, as shown, for example, in FIGS. 1B and 4F. This embodiment will allow the residual bone to be aligned generally collinear with that central axis 26. This embodiment can rely considerably upon the muscles and tissues of the residual limb and lower body to maintain alignment of the residual limb with the prosthesis.

Figure 3F:
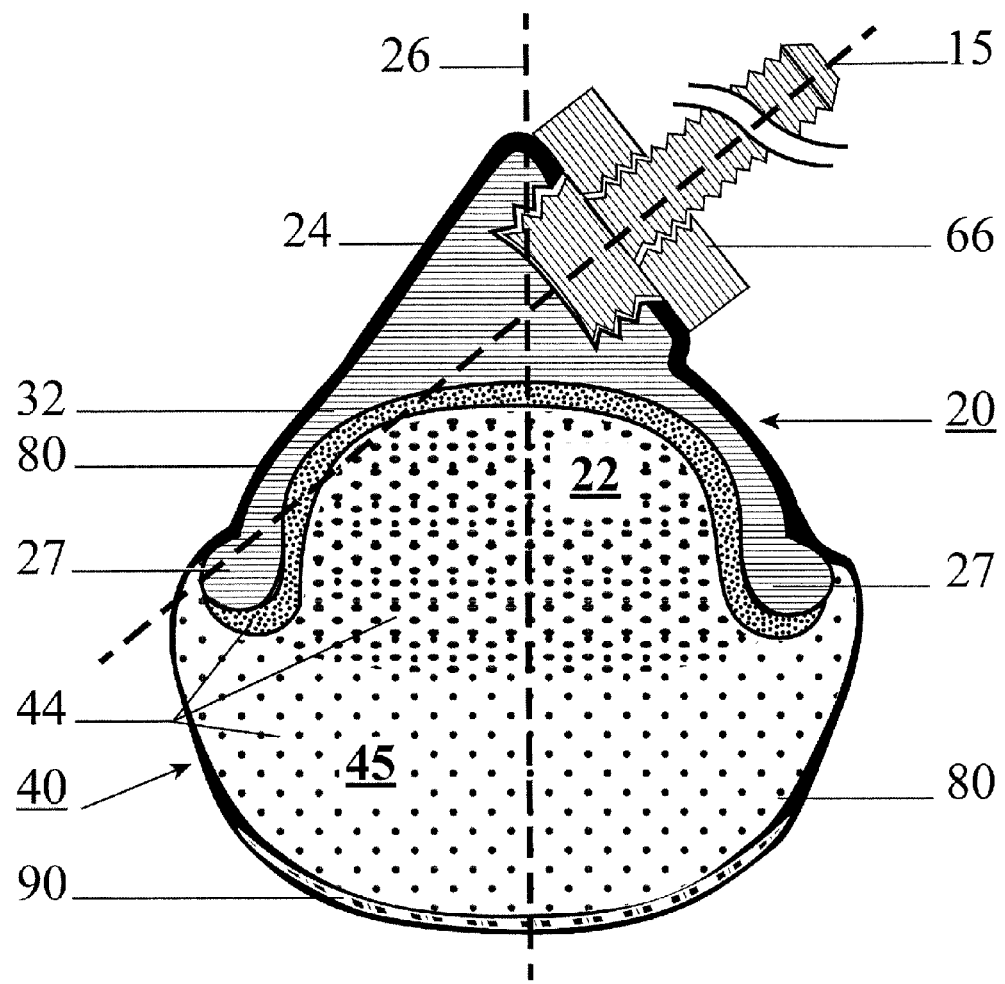
FIG. 3F is a cross-sectional view, along the lateral medial plane shown in FIG. 3C, of an embodiment of a force-distribution support structure having a saddle-shaped support bracket, according to the subject invention. In this embodiment, the bore is tilted away from the central axis of the housing.

In an alternative embodiment, the bore 23 is angled relative to the central axis 26, such that the bore central axis 15 and the central axis 26 are not coaxial. FIG. 3F illustrates an embodiment of a saddle-shaped housing having a bore axis 15 that is tilted away from the central axis 26 of the housing. The bore axis can be tilted to any required angle, depending upon a variety of factors that would be known to a person skilled in the art. In one embodiment, the bore axis is tilted between approximately 10° and approximately 65°. In a specific embodiment, the bore axis is tilted between approximately 25° and 55°. In a particular embodiment, the bore axis is tilted approximately 45° from the central axis of the housing. The bore axis can also be tilted in any direction, depending upon a variety of factors that would be known to a person skilled in the art. In one embodiment, the bore axis is tilted along a lateral plane 500, such as the one shown in FIG. 3C. An example of this embodiment is shown in FIG. 3F. In an alternative embodiment, the bore axis is tilted along a sagittal plane 600, such as the one shown in FIG. 4E. In a particular embodiment, the bore axis is tilted in both a sagittal plane and in a lateral plane direction. When a force-distribution support structure having a saddle-shaped housing with a neck tilted in such fashion, the channel 33 can be non-parallel to the median sagittal plane 600 and can have a superior or inferior direction. In other words, the support bracket can be tilted away from the body and can further have the frontal end or caudal end tilted upwards. A force-distribution support structure having a tilted bore axis can be installed so that the resilient-support faces in a more lateral direction, rather than more coaxial, to the femur. This causes the resilient-support to face at least partially lateral to the body.

When installed onto a terminal bone end, a FDSS having a tilted bore axis can passively direct forces applied to the terminal bone end causing adduction of the residual limb. Adduction of the residual limb, or passive direction of force towards one or more median planes, can aid in maintaining the residual limb in alignment with the body. Advantageously, this passive adduction can also relieve stress on the muscles and tissues of the residual limb and lower body. A further advantage is that the residual limb, and any prosthetic device thereon, can be maintained in a proper alignment often even if the muscles and tissues of the residual limb and lower body are incapable of maintaining such alignment. It should be understood that the alignment of the bore axis can vary depending upon a variety of factors that would be understood by a person skilled in the art, having benefit of the subject disclosure. It should be understood that such variations, which perform the same function, in substantially the same way, with substantially the same result, are within the scope of the subject invention.

As mentioned previously, the quality of the bone and tissues of a residual limb can affect the installation of the embodiments of the subject invention. One of the most important factors is the state of the terminal bone end or residual femur. In order to accommodate an FDSS of the subject invention, the terminal bone end can be reshaped. However, if the bone does not have sufficient length or has an uneven or compromised blunt end, it may be necessary to customize a force-distribution support structure 10 or utilize additional components that can compensate for irregularities. In some instances, it may not be possible for the terminal bone end to be positioned so that it is flush against or abuts the second stem end 64 or a support bracket 20. A secondary component could be employed to provide a platform between the terminal bone end and a support bracket or stem end.

Figure 6:
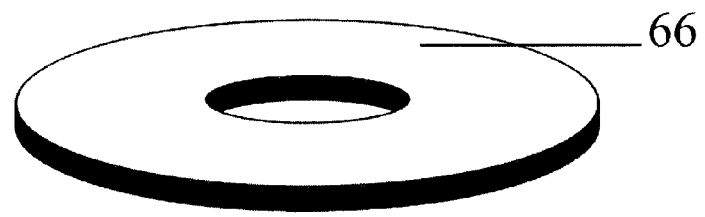
FIG. 6 is a front perspective view of an embodiment of a collar that can be utilized with embodiments of a stem of the subject invention.

In one embodiment, a secondary component is a collar 66 disposed over the first stem end 62. By way of non-limiting example, a collar can be an annular platform that mounts on or over the first end of a stem. FIGS. 1A, 2, and 3F illustrate non-limiting examples of an annular platform collar having a tubular shape. Alternatively, a collar 66 can be a toroidal shaped annular platform that mounts on or over the first end of a stem. In another embodiment, a collar can be similar to a washer, such as shown for example in FIG. 6. In one embodiment, multiple collars can be stacked to provide a customized collar height, as shown, for example, in FIG. 4A. In general, a secondary component can act like a spacer between the terminal bone end and the force-distribution support structure.

In one embodiment, a collar 66 is a rigid structure against which a terminal bone end can abut when the first stem end is installed. In an alternative embodiment, the collar is semi-rigid or can conform, at least slightly, to the shape of the terminal bone end or at least the blunt-end when the first stem end is otherwise installed. In a further embodiment, the collar has a diameter that is greater than the diameter of the second stem end, such that, when the second stem end is operably engaged with a bore 23, the collar can abut, at least partially, against a support bracket. In an alternative embodiment, the collar has a diameter that is at least equivalent to the diameter of a neck 24 on the support bracket, as shown, by way of a non-limiting example, in FIG. 1A. In yet another alternative embodiment, the collar can have a diameter that is equivalent to the second stem end. Likewise, the height of a collar between the proximal end 200 and the distal end 400 can vary depending upon the length of the residual femur, length of the stem first end, shape of the support bracket and other factors that would be known to a person skilled in the art having benefit of the subject disclosure. Other collar diameters, heights, or variations thereof, are within the scope of the subject invention.

If the terminal bone end is not uniform or has a cut-end that is uneven or angled, it can be difficult for a force-distribution support structure 10 of the subject invention to be properly installed. In such instances, the terminal bone end can be reshaped to accommodate embodiments of an FDSS of the subject invention. However, there may be situations in which the terminal bone end cannot be reshaped or cannot be reshaped sufficiently. A collar 66 can be advantageously utilized to provide a customized platform to accommodate all types of terminal bone ends. In one embodiment, multiple collars 66 can be stacked to a desired height. In another embodiment, a collar has a proximal end 200 that is angled to complement an uneven or angled terminal bone end. In another embodiment, the collar has a proximal end that is irregular in shape that inter-digitates with a terminal bone end. In still another embodiment, the proximal end of a collar can be non-rigid or only semi-rigid, so that it can compress and/or conform to be complementary to the shape of a terminal bone end. It would be within the skill of a person trained in the art to determine any of a variety of customizations that can be made to a collar to accommodate various types of terminal bone ends. It should be understood that such variations, which perform the same function, in substantially the same way, with substantially the same results are within the scope of the subject invention.

While the support bracket and stem can provide continuity between the force-distribution support structure 10 and the terminal bone end, the distribution of forces that are applied to the terminal bone end is achieved with a resilient-support 40. In general, a resilient-support is a strong, pliable, elastic, or modifiable structure that protects the tissues of a residual limb from the forces of ambulation exerted by a prosthetic device onto a support bracket. The resilient-support when installed can engender the residual limb, particularly the terminal bone end, with hydraulic features that mimic those found in a normal knee. When fixedly attached to a support bracket, the resilient-support can distribute or re-direct the forces so that they are not exerted onto or are at least minimized on the residual tissue area.

The resilient-support and/or the one or more substances of which it is formed can comprise one or more solids, semi-solids, liquids, semi-liquids, gels, gases, or combinations thereof. Ideally, the resilient-support can comprise one or more materials that have flexible qualities, but which experience minimal or no compression. Thus, while the material may change shape, the volume thereof remains substantially constant. In one embodiment, the resilient-support comprises multiple materials, such that the interior may comprise different materials or different amounts of materials. Further, since the resilient-support can be implanted, the material(s) utilized will preferably be bio-inert or otherwise biocompatible and capable of long-term or permanent in vivo use. Given the subject disclosure, it would be within the skill of a person trained in the art to determine any of a variety of resilient-support designs that can be utilized with the embodiments of the subject invention. It should be understood that variations in the resilient-support that perform the same function, in substantially the same way, with substantially the same result are within the scope of the subject invention.

In one embodiment, the resilient-support is a balloon-like structure comprised of a bladder 41 that can be filled with any of a variety of materials. In a specific embodiment, the exterior bladder 41 comprises a resilient, non-elastic material that allows the shape of the bladder to change, but maintains a constant surface area. In other words, the bladder shape can deform, but the materials inhibit stretching. With this embodiment, the resilient-support can react to forces by adjusting its shape to allow materials within to be redistributed as forces are absorbed. However, the non-elastic, or at least minimally elastic, material of the resilient-support can ensure that the material therein is redistributed within the bladder to absorb and redistribute forces, rather than causing an expansion of the bladder material itself. FIGS. 1A, 2, 3D and 4D illustrate non-limiting examples of such an embodiment.

In a specific embodiment, the bladder is a tough, silicone material that can be filled with any of a variety of liquid, semi-liquid, gel, or other type of viscous material for shock-absorption. For example, the interior 45 of the resilient-support can be filled with, but is not limited to, silicone gel, saline solution, or sterilized water. In a more specific embodiment, the bladder comprises a silicone elastomer that is designed for durability and resistance to puncturing and tearing. Ideally, the bladder can enable the resilient-support to withstand excessive or above-normal forces without failure. In one embodiment, the bladder 41 comprises a silicone material having a durometer of between approximately 75 and approximately 80 on a Shore A scale. Such materials are well-known for their use with other implantable devices, such as breast implants, gluteal implants, or facial implants.

In an alternative embodiment, the bladder comprises a sturdy, flexible or pliable material, such as, for example, corrugated materials, woven fiber materials, and elastic materials, or can be a non-homogeneous combination of materials. In a particular embodiment, the resilient-support comprises a woven, flexible fiber embedded in a strong, flexible silicone elastomer. This embodiment of an embedded fiber weave material can assist in maintaining the shape of the resilient-support when forces are exerted thereon. To further facilitate the ability to resist lateral or rotational forces, the weave direction of the embedded fibers can be diagonal or cross-woven relative to the central axis 26 of the force distribution boot. In certain embodiments described above, the cross-weaving or diagonal weaving can also inhibit unscrewing or other removal of the support bracket 20 from the stem 60.

In a further embodiment, the bladder can have an asymmetric thickness or asymmetrically arranged materials. For example, less elastomer and more reinforcing fiber can be utilized in one area than in another. By way of non-limiting example, a posterior portion can have less reinforcing fiber and more silicone material and, further, have more reinforcing material and less silicone material in the anterior portion, making the anterior portion less flexible, but stronger, and the posterior portion more flexible. Similar techniques can be utilized with other materials of the bladder and/or resilient-support in general. This configuration can be advantageous for patients wherein the applied forces are inconsistent or uneven. As forces are applied, the resilient-support can flex more in the posterior portion and the anterior portion can have less flexibility.

In an alternative embodiment, the bladder 41 can have more elasticity, such that it can stretch or change surface area when forces are applied. This embodiment can have a bladder that comprises a more rigid material or have a more rigidly pre-defined shape. When forces are applied to the bladder, the materials within the interior 45, which can be non-compressible, can respond by redistributing and causing the bladder to expand or stretch in certain places. As the forces lessen, the interior materials redistribute allowing the bladder to return to the pre-defined shape and/or to expand or stretch in a different area.

In another embodiment, the resilient-support is a solid or semi-solid material that has sufficient elastic properties to absorb applied forces. In a further embodiment, the resilient-support is a homogeneous material that can be compressed, stretched, deformed, or otherwise change shape to distribute forces. This can include, by way of non-limiting examples, rubber, silicone, semi-solid gel matrix, foam, or similar materials. In an alternative embodiments, the resilient-support can be a solid or semi-solid, non-homogenous material comprising two or more substances. The combined materials can provide different elastic properties for absorbing applied forces.

In a further alternative embodiment, the resilient-support can be a solid of varying density that can have different compressible, non-compressible, and/or elastic properties in different areas. Thus, in one embodiment, the resilient-support has in interior 45 that becomes increasingly dense or solid towards the interior, so that it has layers 44 of increasing resistance against applied forces. In one embodiment, the resilient-support is a homogeneous material that exhibits gradual, increasing density towards the interior or nearer to a support bracket 20. In an alternative embodiment, the resilient-support is a non-homogeneous solid comprised of two or more materials that graduate into an increasingly less elastic and less resilient material. FIGS. 1A, 3D and 4D illustrate examples wherein the interior 45 of the resilient-support comprises material that is less dense, more elastic, nearer the distal end and more dense, less elastic, nearer the proximal end.

In a further embodiment, a resilient-support comprises at least one outer material that can provide resistance and an internal material that provides greater resistance to more extreme forces applied to the resilient-support. Further alternative embodiments can include successive layers 44 of increasingly resistant materials. In certain embodiments, two or more materials can be layered to provide increasing resistance. FIGS. 1A, 3D and 4D show non-limiting examples of how different density materials can be arranged in layers 44 over, around, and within the hollow areas of a support bracket to provide increasing resistance to applied forces. FIGS. 3D and 4D also illustrate how material is incorporated into grooves 12 or around protrusions 14, to secure a resilient-support.

In a specific embodiment, a resilient support comprises three distinct layers. A first layer of material nearest the support bracket can have a durometer of between approximately 40 to approximately 60 on a Shore A scale. A second, more distal layer can have a durometer of between approximately 25 to approximately 45 on a Shore A Scale. A third layer can have a durometer of between approximately 20 to approximately 30 on a Shore A scale. Alternative embodiments can have additional layers with varying durometers. For example, a fourth layer material of having a durometer of between approximately 0 (complete fluid) to approximately 20 (gel) on a Shore A scale can be utilized at the most distal end. Alternative embodiments can also utilize materials with a higher durometer nearest the distal end and materials of a lower durometer nearest the proximal end.

The arrangement of one or more layers of material, of varying durometers, in a resilient-support can depend upon on a variety of factors that would be understood to a person skilled in the art. While the embodiments described and shown herein describe layers of successive density from approximately the distal end to approximately the proximal end, certain circumstances and amputee requirements may necessitate layers having a more vertical or tilted orientation. The point is that alternative arrangements of resilient-support materials providing substantially the same function, in substantially the same way, with substantially the same result, are considered to be within the scope of the subject invention. Resilient-support materials of any desired durometers can also be utilized and are within the scope of the present invention.

In a yet further alternative embodiment the resilient-support can be a combination of a filled bladder 41 and one or more of the solid and/or semi-solid/variable density embodiments described above. With this embodiment a solid or semi-solid variable density component can be employed nearer to a support bracket. A filled bladder structure can then be utilized against the solid or semi-solid variable density component. This arrangement of a resilient-support can more closely mimic the structure and hydraulic function of a natural joint.

The overall, outward, shape of a resilient-support will vary depending upon the shape of the support bracket, the type and location of the stem, the shock-absorbing materials being used, the shape and integrity of a residual limb, and a variety of other factors that would be known to those with skill in the art. In one embodiment, a thicker layer of shock-absorbing material is used at the more distal end 400 of the support bracket, which is shown as a non-limiting example in FIGS. 1A and 4D. In an alternative embodiment, there is a thicker layer of shock absorbing material below the more frontal end 250 and/or more caudal end 450, which is shown as a non-limiting example in FIG. 4A. In a further embodiment, the shape of the support bracket can be such that it causes more or less shock-absorbing material to be located at certain areas. As a non-limiting example, the housing shown in FIG. 1E can have a thicker layer of shock-absorbing material near the lip 27. FIGS. 4A and 4B illustrate an embodiment where the sidewalls 32 have one or more indentations 33, so that there can be more of the resilient-support 40 and, thus, a thicker padding of shock-absorbing material closer to the frontal end and/or the caudal end of the support bracket.

Because a support bracket can comprise a significantly rigid material, it can be important to ensure that the residual tissues are protected from direct contact with any part of the support bracket that has the capacity to exert tissue-damaging force. Once installed, the most distal edges, or lip 27, of a support bracket 20 has the potential to cause damage to residual tissues, if not protected. Thus, it can be important for some portions of a support bracket to be particularly protected against contact with tissues. In one embodiment, the resilient-support overlaps or covers the distal end of a support bracket, which can include the lip 27 and the frontal end and/or the caudal ends. This can ensure that where the support bracket is likely to exert force against residual tissue, there will be at least some amount of shock absorbing material to buffer that contact. FIGS. 1A, 2, 3A, and 4B provide non-limiting examples of how a resilient-support 40 can surround the distal, frontal, and/or caudal ends of a support bracket and also overlap the lip to reduce or prevent force exerting surfaces of the support bracket from direct contact with residual tissues.

To further ensure that the support bracket is inhibited from direct contact with the residual tissues, the attachment of the resilient-support should be secure and capable of maintaining the correct position of the resilient support. Particularly since the embodiments of the subject invention are typically utilized in vivo, a secure attachment of the resilient support to the support bracket is important.

As discussed above, a resilient-support can have layers 44 of varying durometers, such that there can be increasing force resistance nearer the support bracket. In one embodiment, each layer is independently fixedly attached to the support bracket. In a further embodiment, each layer is independently fixedly attached to another layer of the resilient-support. Alternatively, there can be a first layer fixedly attached to the support bracket and subsequent layers can be fixedly attached to the first layer or other successive layers. With this embodiment, layers can be fixedly attached with any of a variety of adhesive products or by mechanical components, as mentioned above.

In an alternative embodiment, successive layers 44 can be welded or seamlessly formed as a single unit. For example, layers comprised of the same, similar, or compatible materials can be heat sealed together. This could be accomplished during the manufacturing process or as a secondary process after layers are formed. FIG. 3D illustrates an example of an embodiment where a first layer 44 can be formed on the interior of a housing. Note the grooves 12 within the housing that can further hold the first layer against the housing. A successive layer material, of lower durometer, can then be introduced within the interior of the housing, followed by a still lower durometer layer material at the most distal end. Where two or more layers meet, the materials can mingle or mix, becoming seamlessly joined, such as shown, in the non-limiting example, in FIG. 3D.

One advantage of the embodiments of the subject invention is the modularity of the components, which allows them to be upgraded, replaced, or repaired if necessary. As described above, in certain embodiments, the support bracket can be removed from the stem. It can also be beneficial if additional modularity is enabled by the resilient-support being removable from the support bracket. Alternatively, where the resilient-support comprises more than one layer, individual layers could be removed, replaced, alternated, or changed if necessary. In a still further embodiment, the resilient-support, or layers thereof, could be removed or replaced without removing the support bracket from the stem.

To facilitate removal or alteration of a resilient-support, the FDSS 10, or some part thereof, can be covered by a sleeve 80 that surrounds the resilient-support and secures it to at least part of a support bracket. A sleeve can be comprised of any of a variety of one or more materials having sufficient strength and flexibility. Ideally, the sleeve does not inhibit the operation of the resilient-support or the support bracket. The sleeve should also be able to withstand the forces exerted on the force-distribution support structure 10. The sleeve can also act as a protective cover for the resilient-support and support bracket.

A sleeve 80 can be comprised of any of a variety of one or more materials. The factors that can be considered by those skilled in the art with regard to the choice of materials for a bladder 41 of the subject invention have been discussed above and are reasserted here with regard to a sleeve. In a particular embodiment, the sleeve is comprised of one or more pliable materials capable of covering and/or securing at least a portion of a force-distribution support structure 10, including a resilient support. In one embodiment, the sleeve comprises a pliable, non-elastic material that can react to changes in shape of the resilient support. With this embodiment, the sleeve can experience minimal stretching and can maintain a substantially constant surface area. In an alternative embodiment, a sleeve is comprised of an elastic material that can be fitted over a force-distribution support structure. In an alternative embodiment, a sleeve material, whether elastic or inelastic can be formed over the force-distribution support structure. In this embodiment, the assembled FDSS, or just the support bracket and operably attached compressible support are dipped into or coated with a material that adheres to the device and fills spaces to create a form-fitted sleeve. With this embodiment, the sleeve is not intended to be removed intact. In a particular embodiment, the assembled FDSS, or a part thereof, is coated with a silicone material that is flexible, resilient, and can add an additional layer of shock-absorbing material.

In a specific embodiment, a sleeve 80 comprises a silicone material. In a further specific embodiment, the sleeve comprises a silicone material having a durometer of between approximately 75 and approximately 85 on a Shore A scale. In a still further specific embodiment, the sleeve is formed over the FDSS by one or more immersions while the silicone is in a liquid or semi-liquid form.

A sleeve 80 can have a uniform thickness such that it provides complete coverage where it contacts a resilient-support and a support bracket. Alternatively, a sleeve can have varying thickness such that some areas have more or less material. In another embodiment, a sleeve can have one or more regular or irregular apertures, giving it a net-like or mesh appearance, such that it provides incomplete or partial coverage over a resilient-support and a support bracket.

In one embodiment, a sleeve 80 covers the entire resilient-support 40 and at least part of a support bracket 20 attached thereto. FIG. 3D illustrates an example of this embodiment. In an alternative embodiment, the sleeve covers the entire resilient-support and the support bracket, including a neck 24, if present. FIGS. 1A, 3F, and 4D illustrate examples of sleeve embodiments that cover most or all of a FDSS, including a neck.

In one embodiment, the sleeve covers an already operably attached support bracket and resilient-support. In another embodiment, the sleeve can be utilized to operably attach a support bracket and resilient-support. In this embodiment, the sleeve can hold and secure the resilient-support in position against a support bracket. In a further alternative embodiment, the resilient-support is partially operably attached to the support bracket and the sleeve is employed to enhance or further operably attach the resilient-support to the support bracket.

A sleeve can also provide an efficacious means for protecting a FDSS from a bioenvironment. It can also contribute to the overall structure by securing, or at least supporting, a resilient-support and a support bracket. A person with skill in the art, having benefit of the subject disclosure, would be able to determine any of a variety of sleeve designs and one or more appropriate materials for a sleeve. Such alternative sleeve modifications, which perform the same function, in substantially the same way, to provide substantially the same result, are within the scope of the subject invention.

Figure 7:
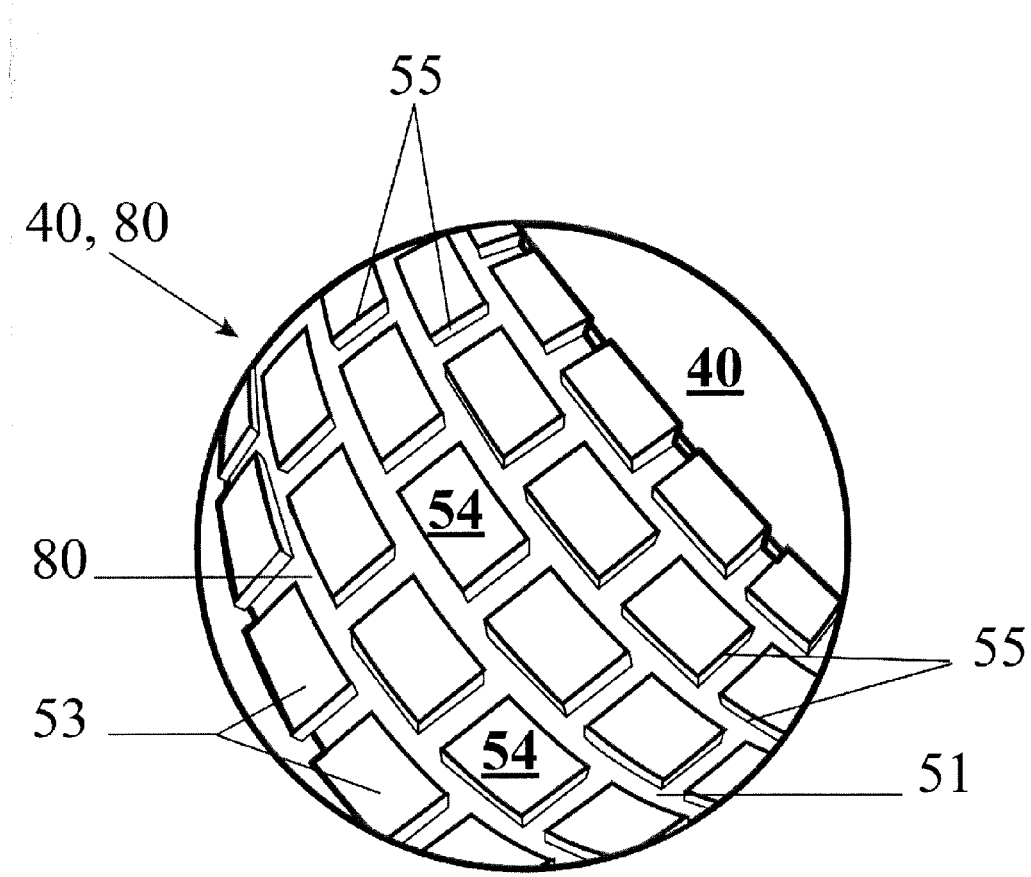
FIG. 7 illustrates an enlarged view of an embodiment of the external surface of a resilient-support with tiles.

The embodiments of the subject invention are intended to absorb and dissipate forces applied to a residual limb, in particular, forces applied to the terminal end. However, it is possible that too much force, particularly concentrated force, i.e., a force applied over a small area, can cause damage, such as a puncture, to the sleeve and/or the resilient-support. To protect against these types of concentrated forces, a plurality of rigid or, at least, semi-rigid tiles 53 can be arranged on the exterior of the force-distribution support structure. In one embodiment, a tile has a contact surface 54 and one or more lateral surfaces 55. In a still further embodiment, a plurality of tiles can be arranged on the outer surface of a resilient-support 40 or a sleeve 80, so that their lateral surfaces 55 can abut against one another when force is applied to the sleeve. It is also possible for tiles to be utilized on both a sleeve and a resilient support, if desired. In one embodiment, the tiles are fixedly attached to an outer surface of the force-distribution support structure. In this embodiment, the tiles can be separate components fixedly attached or they can be formed as part of the material itself, such as, for example, the way that knobby treads are formed on tires. In an alternative embodiment, the tiles are individual or grouped components that are partially embedded within the material of the sleeve, so that they are fixedly attached with their contact surfaces 54 facing outward from the FDSS. FIG. 7 illustrates an embodiment of an outer surface of a sleeve or resilient-support having a plurality of tiles.

The application of force can cause the compressible support, and a sleeve if utilized, to flex inwards or towards the support bracket, distributing the force to the internal shock-absorbing material. The tiles can act as a further shock-absorbing structure and can also prevent punctures to the sleeve and/or underlying layers of shock-absorbing material 44. When a concentrated force is applied to a resilient-support or a sleeve having tiles thereon, the sleeve and the compressible support can still flex inward. However, the rigid, or semi-rigid, tiles arranged at a pre-determined distance from each other, will also move inward with the force. The stronger or harder the force applied, the further inward one or more tiles move, and the closer they come together until their lateral surfaces 55 abut against each other. When two or more tiles abut against each other, they can prevent that part of the sleeve and/or resilient-support to which they are attached from continuing to flex or bend inwards. If force continues to be applied to the same area, other surrounding portions of the sleeve will also begin to flex inward, again, until the lateral sides of the tiles attached to that portion of the sleeve abut each other. As long as force continues to be increasingly applied to the same area, more tiles will continue to flex inward until they abut against each other, causing more and more area of the sleeve to flex inward and distributing the force over a larger area.

Tiles can have any of a myriad of shapes, including, but not limited to, rectangular, as shown, for example, in FIG. 7, square, triangular, circular, oval, or any other polygonal shape. The arrangement of the tiles and the distance therebetween can affect the amount of flexion. In a further embodiment, the lateral surfaces 55 can be slanted so that they can control or affect the direction of flexion. In one embodiment, the tiles have at least four sides, such that they are generally square or rectangular. In a further embodiment, the tiles are arranged in linear rows with the tiles of one row staggered with the tiles of an adjacent row, an example of which is shown in FIG. 7. A person with skill in the art would be able to determine alternative configurations and arrangements of tiles to suit a particular purpose. It should be understood that such alternative embodiments, which perform the same function, in substantially the same way, to provide substantially the same result, are within the scope of the subject invention.

Particular circumstances may dictate that a resilient support be subject to less flexibility or be protected from certain types of applied force. External prosthetic devices are capable of exerting powerful forces against a force distribution support structure. These types of forces can necessitate that a resilient-support be protected against instantaneous forces or excessive shock. The tiles 53 described above can provide puncture resistance and can assist in distributing forces on a resilient-support. But, the tiles allow a resilient-support to maintain flexibility over a smaller area.

An alternative embodiment employs a rigid plate 90 fixedly positioned at, or about, the distal end of a force-distribution support structure. In a further embodiment, a rigid plate 90 is emplaced so that it can act on distal portion 400 of a resilient-support. In one embodiment, a rigid plate is fixedly emplaced within a distal portion of a sleeve 80. FIGS. 1A, 2, and 4D illustrate embodiments of a rigid plate 90 within the distal end of a sleeve. In an alternative embodiment, a rigid plate is fixedly attached at or about the distal end of the resilient support. The rigid plate can be fixedly attached within the resilient support, or it can be fixedly attached to the resilient-support 40. FIGS. 3A, 3D and 3F illustrate an embodiment of rigid support fixedly engaged with a layer 44 of the resilient support and covered by the sleeve 80.

The shape of a rigid plate can depend upon a variety of factors, including, but not limited to, the shape of the support bracket. In an embodiment, a rigid plate has a shape that is functionally compatible with a support bracket. In a specific embodiment, utilizing a bell-shaped housing, the rigid plate can be substantially circular or oval, such that it is generally in the shape of the lip 27 portion of the housing. In another specific embodiment, utilizing a saddle-shaped housing, a rigid plate is elongated and is generally in the shape of the channel 33. In one embodiment, a rigid plate is imparted with convex curvature towards the distal end 400 of a FDSS.

When force is applied to a rigid plate, the plate moves, relative to the applied force, towards the support bracket, causing a significant portion of the resilient-support to respond. During ambulation, forces typically move, or "rock," from the posterior to the anterior of a residual limb. As described above, embodiments of the subject invention can experience a similar posterior to anterior movement of applied force. An embodiment of the subject invention having a rigid plate would have the posterior end of a rigid plate first move towards the resilient-support, followed by a more central portion and finally a more anterior portion. As the rigid plate 90 pushes against the resilient-support, the resilient-support can flex and the material thereof redistribute away from that area of the rigid plate. The greater the area of a rigid plate affected by the force, the more of the resilient-support material that reacts to absorb the forces. For larger, or more vigorously active, amputees, this can be advantageous, since it would engage a larger portion of the resilient-support during ambulation.

As the above-description shows, the devices and methods of the subject invention represent a unique improvement to the area of prosthetic devices. They have the ability to improve the quality of a residual limb and reduce the amount of force applied to tissues ill-equipped to handle such forces. The devices and methods of the subject invention can also restore the role of the axial skeleton in ambulation and force absorption. All of these factors can improve the success of an amputee with using an external prosthetic device and can improve an overall improved quality of life.

The scope of the invention is not limited by the specific examples and suggested procedures and uses related herein since modifications can be made within such scope from the information provided by this specification to those skilled in the art.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

The examples and embodiments described herein are for illustrative purposes only and that various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and that various modifications, both as to equipment details and operating procedures can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

I claim:

1. An implantable prosthetic device for attachment to a terminal bone end comprising: a stem having first and second ends, the first end for attachment to the terminal bone end, wherein the first end is configured to be introduced into intramedullary bone space, wherein the first end further comprises holes to promote bone ingrowth; a support bracket comprising a housing having a proximal end and a distal end with a hollow interior therein, a bore at the proximal end for receiving the second end of the stem, and a lip at the distal end; and a resilient support fixedly attached to the hollow interior and extending from the distal end of the support bracket to cover at least the lip at the distal end, wherein the resilient support comprises distinct layers of semi-solid elastic material, wherein a first layer is secured at least partially to the hollow interior of the housing, further comprising additional layers that are progressively less dense towards the distal end of the support bracket, wherein the layers of the resilient support comprise material of different durometers.

2. An implantable prosthetic device according to claim 1, wherein the first end of the stem comprises threading.

3. An implantable prosthetic device according to claim 2, wherein the first end of the stem comprises self-tapping continuous threading.

4. An implantable prosthetic device according to claim 2, wherein the second end of the stem comprises threading.

5. An implantable prosthetic device according to claim 4, wherein the bore in the support bracket comprises threading compatible with the threading on the second end of the stem.

6. An implantable prosthetic device according to claim 5, further comprising a neck at about the proximal end of the housing, wherein the bore is disposed within the neck.

7. An implantable prosthetic device according to claim 6, wherein the bore has an axis that is parallel to a central axis of the housing.

8. An implantable prosthetic device according to claim 6, wherein the bore has an axis that is tilted away from a central axis of the housing.

9. An implantable prosthetic device according to claim 8, wherein the bore is tilted at an angle that is capable of controlling abduction of the terminal bone end.

10. An implantable prosthetic device according to claim 6, further comprising a groove, protrusion, or orifice to which the resilient support can form a complimentary attachment that secures the resilient support to the hollow interior.

11. An implantable prosthetic device according to claim 1, further comprising a chamber within the first end of the stem that is contiguous with the holes in the first end.

12. An implantable prosthetic device according to claim 11, further comprising a flute within the first end of the stem.

13. An implantable prosthetic device according to claim 1, further comprising a sleeve covering the resilient support and at least partially the housing.

14. An implantable prosthetic device according to claim 13, wherein the sleeve comprises an elastic material.

15. An implantable prosthetic device according to claim 14, wherein the sleeve comprises silicone.

16. An implantable prosthetic device according to claim 13, further comprising a rigid plate fixedly attached at or about the distal end of the resilient support.

17. An implantable prosthetic device according to claim 16, wherein the rigid plate is fixedly attached to one or more layers at the distal end of the resilient support.

18. An implantable prosthetic device according to claim 16, wherein the rigid plate is fixedly emplaced within the sleeve at the distal end of the resilient support.

19. An implantable prosthetic device according to claim 16, wherein the housing is a bell-shaped housing.

20. An implantable prosthetic device according to claim 19, wherein the housing has a lip that is level on all sides.

21. An implantable prosthetic device according to claim 19, wherein the housing has a lip that is not completely level on all sides.

22. An implantable prosthetic device according to claim 16, wherein the housing is a saddle-shaped housing having at least two sidewalls between a frontal end and a caudel end.

23. An implantable prosthetic device according to claim 22, wherein the distal end of at least one sidewall is curved between the frontal end and the distal end.

24. An implantable prosthetic device according to claim 23, wherein the distal end of at least one sidewall has a multi-curvate shape.

25. An implantable prosthetic device according to claim 23, further comprising one or more indentations within at least one sidewall.

26. An implantable prosthetic device according to claim 13, further comprising a plurality of tiles arranged on an exterior surface at the distal end of the resilient support.

27. An implantable prosthetic device according to claim 26, wherein the tiles are arranged on an exterior surface of the resilient support.

28. An implantable prosthetic device according to claim 26, wherein the tiles are arranged on an exterior surface of the sleeve.

29. An implantable prosthetic device according to claim 26, wherein the housing is a bell-shaped housing.

30. An implantable prosthetic device according to claim 29, wherein the housing has a lip that is level on all sides.

31. An implantable prosthetic device according to claim 29, wherein the housing has a lip that is not completely level on all sides.

32. An implantable prosthetic device according to claim 26, wherein the housing is a saddle-shaped housing having at least two sidewalls between a frontal end and a caudel end.

33. An implantable prosthetic device according to claim 32, wherein the distal end of at least one sidewall is curved between the frontal end and the distal end.

34. An implantable prosthetic device according to claim 33, wherein the distal end of at least one sidewall has a multi-curvate shape.

35. An implantable prosthetic device according to claim 34, further comprising one or more indentations within at least one sidewall.

36. An implantable prosthetic device according to claim 1, further comprising a collar disposed around the bore.

37. An implantable prosthetic device according to claim 1, further comprising one or more anchoring screws.

* * * * *